(12) United States Patent
Koga

(10) Patent No.: US 9,239,252 B2
(45) Date of Patent: Jan. 19, 2016

(54) SENSOR CONTAINER, SENSOR INFORMATION MANAGEMENT METHOD USING THE SAME, AND SENSOR INFORMATION MANAGEMENT SYSTEM FOR MANAGING SENSOR HOUSED IN SENSOR CONTAINER

(71) Applicant: PANASONIC HEALTHCARE HOLDINGS CO., LTD., Minato-ku, Tokyo (JP)

(72) Inventor: Yuiko Koga, Ehime (JP)

(73) Assignee: PANASONIC HEALTHCARE HOLDINGS CO., LTD., Minato-Ku, Tokyo (JP)

( * ) Notice: Subject to any disclaimer, the term of this patent is extended or adjusted under 35 U.S.C. 154(b) by 55 days.

(21) Appl. No.: 14/365,105

(22) PCT Filed: Dec. 26, 2013

(86) PCT No.: PCT/JP2013/007650
§ 371 (c)(1),
(2) Date: Jun. 13, 2014

(87) PCT Pub. No.: WO2014/103322
PCT Pub. Date: Jul. 3, 2014

(65) Prior Publication Data
US 2015/0268070 A1 Sep. 24, 2015

(30) Foreign Application Priority Data

Dec. 27, 2012 (JP) ................. 2012-284192
Feb. 5, 2013 (JP) ................. 2013-020148
Mar. 11, 2013 (JP) ................. 2013-047498
Apr. 23, 2013 (JP) ................. 2013-089973

(51) Int. Cl.
*G01D 11/24* (2006.01)
*G01N 33/48* (2006.01)
(Continued)

(52) U.S. Cl.
CPC ............. *G01D 11/245* (2013.01); *G01D 13/00* (2013.01); *G01N 33/48* (2013.01);
(Continued)

(58) Field of Classification Search
CPC .............................. G01N 33/48; G01D 11/24
USPC .......................................................... 73/431
See application file for complete search history.

(56) References Cited

U.S. PATENT DOCUMENTS 7,818,132 B2  10/2010  Pritchard et al.
8,210,349 B2   7/2012  Yamaoka
(Continued)

FOREIGN PATENT DOCUMENTS

GB  WO 2006131697 A2 * 12/2006 ......... A61B 5/14532
JP  2002-156358 A    5/2002
(Continued)

OTHER PUBLICATIONS

International Search Report of Int'l Appln. No. PCT/JP2013/007650 issued on Apr. 15, 2014.
(Continued)

*Primary Examiner* — Lisa Caputo
*Assistant Examiner* — Jamel Williams
(74) *Attorney, Agent, or Firm* — Shinjyu Global IP

(57) ABSTRACT

A sensor container includes a container body having an opening portion, a lid that covers the opening portion of the container body, and a plurality of sensors for measuring biological information that are housed in the container body. The container body or the lid has a mark that includes information indicating the usable period of the sensors starting from a point in time when the lid is released from the container body. The mark is covered with a removable seal.

25 Claims, 14 Drawing Sheets

(51) Int. Cl.
*G01N 33/487* (2006.01)
*G01D 13/00* (2006.01)
*A61B 5/15* (2006.01)

(52) U.S. Cl.
CPC .... *G01N 33/48771* (2013.01); *A61B 5/150305* (2013.01); *A61B 5/150786* (2013.01); *A61B 2562/0295* (2013.01); *A61B 2562/242* (2013.01)

(56) References Cited

U.S. PATENT DOCUMENTS

| | | |
|---|---|---|
| 8,318,096 B2 | 11/2012 | Okuda et al. |
| 2006/0094986 A1 | 5/2006 | Neel et al. |
| 2006/0191813 A1 | 8/2006 | Yamaoka |
| 2009/0119024 A1 | 5/2009 | Pritchard et al. |
| 2010/0035334 A1 | 2/2010 | Okuda et al. |

FOREIGN PATENT DOCUMENTS

| | | |
|---|---|---|
| JP | 2004-115085 A | 4/2004 |
| JP | 2008-180583 A | 8/2008 |
| JP | 2009-512858 A | 3/2009 |
| JP | 2009-198491 A | 9/2009 |
| JP | 2010-025728 A | 2/2010 |
| JP | 2010-127786 A | 6/2010 |
| JP | 2010-281845 A | 12/2010 |
| JP | 2011-184080 A | 9/2011 |
| JP | 2012-078109 A | 4/2012 |
| JP | 2012-132938 A | 7/2012 |
| JP | 2012-141315 A | 7/2012 |
| WO | 2007/050396 A1 | 5/2007 |

OTHER PUBLICATIONS

Office Action from the corresponding Japanese Patent Application No. 2014-524597 issued on Jun. 2, 2015.
Arkray, Instruction Manual for GLUCOCARD G+meter GT-1820 published in 2007, and revised on Apr. 2012, p. 23.

* cited by examiner

FIG. 5
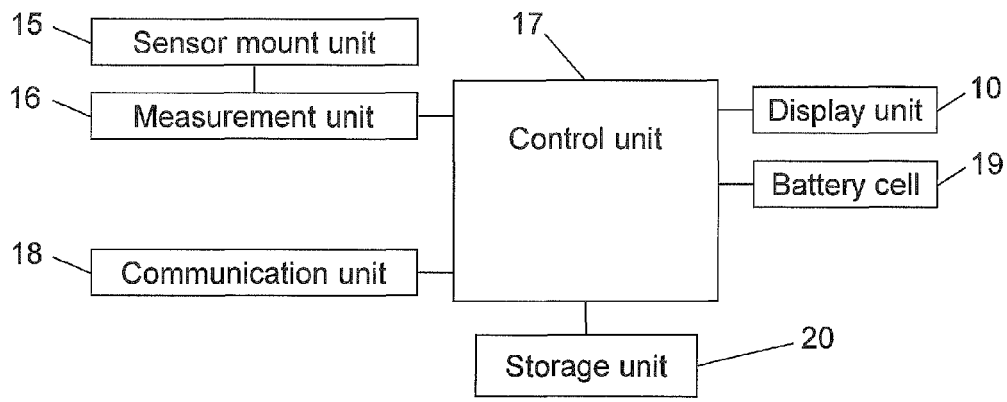
FIG. 6
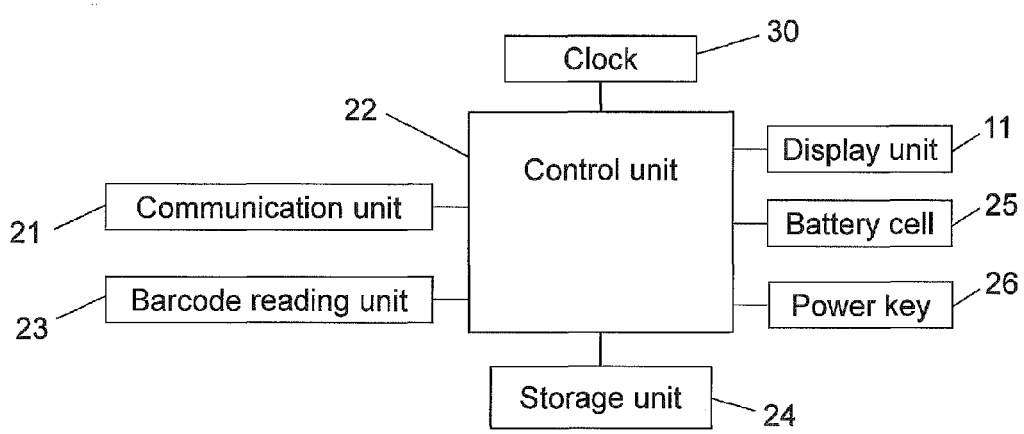
FIG. 7
(a)
| Barcode information | |
|---|---:|
| Number of initially housed sensors | 30 |
| Manufacture date | 2012/12/10 |
| Validity expiration date | 2014/3/10 |
| Usable period | 90 days |
(b)
| Sensor information | |
|---|---:|
| Number of sensors | 30 |
| Use start date | 2013/1/1 |
| Usable period | 90 days |

| Barcode information | |
|---|---|
| Number of initially housed sensors | 30 |
| Identification information | ***** |
| Manufacture date | ***** |
| Validity expiration date | ***** |
| Usable period | 90 days |

(a)

| Container information | | |
|---|---|---|
| Identification information | 201A | 201B |
| Number of sensors | 12 | 30 |
| User start date | 2012/12/1 | 2013/1/10 |
| Usable period | 90 days | 90 days |

(b)

| Barcode information | |
|---|---|
| Number of initially housed sensors | 30 |
| Identification information | ***** |
| Manufacture date | ***** |
| Validity expiration date | ***** |
| Usable period | 90 days |

(a)

| Container information | | |
|---|---|---|
| Identification information | 201A | 201B |
| Number of sensors | 5 | 30 |
| User start date | 2012/12/1 | 2013/1/10 |
| Usable period | 90 days | 90 days |
| Manufacture date | 2012/8/15 | 2012/4/5 |
| Validity expiration date | 2013/11/5 | 2013/7/5 |

SENSOR CONTAINER, SENSOR INFORMATION MANAGEMENT METHOD USING THE SAME, AND SENSOR INFORMATION MANAGEMENT SYSTEM FOR MANAGING SENSOR HOUSED IN SENSOR CONTAINER

PRIORITY

This application claims priority under 35 U.S.C. §120 and 35 U.S.C. §365 of International Application PCT/JP2013/007650, with an international filing date of Dec. 26, 2013 which claims priority to Japanese Patent Application No. JP2013-089973 filed on Apr. 23, 2013, Japanese Patent Application No. JP2012-284192 filed on Dec. 27, 2012, Japanese Patent Application No. JP2013-020148 filed on Feb. 5, 2013, and Japanese Patent Application No. JP2013-047498 filed on Mar. 11, 2013. The entire disclosures of International Application PCT/JP2013/007650 and Japanese Patent Application Nos. JP2013-089973, JP2012-284192, JP2013-020148, and JP2013-047498 are hereby incorporated herein by reference.

TECHNICAL FIELD

The present disclosure relates to a sensor container for housing sensors for measuring biological information such as a blood glucose level, a sensor management method using the sensor container, and a sensor information management system for managing the sensors housed in the sensor container.

BACKGROUND

A sensor container in a conventional example includes a container and sensors, which are housed in the container, for measuring biological information. If, for example, it is a sensor container for housing sensors for measuring a blood glucose level, information related to the sensors housed in the sensor container (e.g., the number of initially housed sensors, the production management number of the sensors, information on the validity period of the sensors based on the manufacture date, etc.) is stored in an electronic tag attached to the container.

The sensors in the sensor container are managed by a blood glucose level measuring device reading the information related to the sensors (e.g., Patent Literature 1: JP 2012-78109A).

SUMMARY

A problem of the aforementioned conventional example lies in that the sensors are not user-friendly. That is to say, if, for example, the sensor container in the conventional example is for housing sensors for measuring a blood glucose level, information indicating the period of time during which the measurement function of the sensors housed in this sensor container operates validly is displayed by the blood glucose level measuring device. Here, the period of time during which the measurement function of the sensors operates validly is indicated by a validity period and a usable period, for example.

The validity period indicates the period of time during which the measurement function of the sensors operates validly, starting from the manufacture date of the sensors. The usable period indicates the period of time during which the measurement function of the sensors operates validly, starting from a use start date, which is the date on which a sensor is first taken out of an unused sensor container. That is to say, such a usable period is set since the measurement function of the sensors for measuring a blood glucose level deteriorates if the sensors are exposed to the air for a long period of time. In practical use, usually a user prepares a spare sensor container so as to address the case of running out of the sensors.

In a situation where the validity period or the usable period of the sensors is thus set, a user attempts to take a sensor out of a sensor container that is in use and use the sensor. However, as mentioned above, in a situation where there are a plurality of sensor containers including the spare sensor container, the user cannot distinguish the sensor container in use from other sensor containers, resulting in poor user-friendliness.

Therefore, an object of the present disclosure is to make sensors for measuring biological information more user-friendly.

According to a first aspect of the present disclosure, a sensor container comprises: a container body having an opening portion, a lid configured to cover the opening portion of the container body; and one or more sensors for measuring biological information, the one or more sensors being housed in the container body. The container body or the lid includes a mark having information indicating a usable period of the one or more sensors starting from a point in time when the lid is released from the container body. The mark is covered with a removable seal.

According to a second aspect of the present disclosure, a sensor information management system comprises: a sensor container including a container body having an opening portion and a lid configured to cover the opening portion of the container body, a plurality of sensors for measuring biological information being housed in the container body; a biological information measuring device configured to mount thereon the sensors housed in the sensor container; and a communication terminal configured to communicate with the biological information measuring device and receive a measured value obtained by the biological information measuring device. The sensor container indicates, on the container body or the lid, a mark having sensor information containing individual identification information of the sensor container, information indicating a number of sensors that are initially housed in the container body, and information indicating a usable period of the sensors starting from a point in time when the lid is released from the container body. The communication terminal includes a sensor information reading unit operable to read the mark, a storage unit operable to store the sensor information acquired from the mark, a display unit configured to display the sensor information stored in the storage unit, and a control unit operable to acquire the sensor information from the storage unit and cause the display unit to display the acquired sensor information. The control unit further causes the storage unit to store the number of sensors acquired by decreasing a number of the housed sensors each time the control unit of the communication terminal receives the measured value from the biological information measuring device, and causes the display unit to display the acquired number of sensors.

As described above, in the sensor container according to the present disclosure, the usable period mark that sets the usable period of the sensors from the point in time when the lid is released from the container is provided on the container or the lid, and this usable period mark is covered with a removable seal. For this reason, when a user uses an unused sensor container, the user removes the seal and checks the usable period mark. With this usable period mark, the user can become aware of the usable period of the sensors for measuring a blood glucose level. Furthermore, at this time, it is indicated that the sensor container is in use, as a result of the seal having been torn off, and the user can distinguish this sensor container from an unused sensor container covered with the seal. Accordingly, the user can take a sensor out of the sensor container in use and use this sensor, and consequently the sensors can be made more user-friendly.

Since sensors for measuring biological information that are housed in such a sensor container are susceptible to light, the sensor container is made of a light-blocking material, and in many cases, the state of the housed sensors cannot be checked from the outside in a state in which the lid of the sensor container is closed. In this situation, in order to check the accurate number of sensors in the sensor container, it is necessary for the user to open the lid of the sensor container and count the number of sensors every time, and therefore the sensors are not user-friendly in this aspect.

Therefore, in the sensor information management system according to the present disclosure, every time biological information is measured by the biological information measuring device and the measured value thereof is sent to the communication terminal, the communication terminal acquires the accurate number of sensors in the sensor container and displays that number of sensors on the display unit. Accordingly, the user can become aware of the accurate number of sensors in the sensor container, and the sensors are made more user-friendly in this aspect as well.

BRIEF DESCRIPTION OF DRAWINGS

FIG. 5 is a control block diagram of the biological information measuring device according to Embodiment 1.

FIG. 6 is a control block diagram of a mobile terminal according to Embodiment 1.

FIG. 7 is a diagram showing the content of barcode information of the sensor container and sensor information of the mobile terminal according to Embodiment 1.

FIG. 22 is a diagram showing the content of barcode information of a sensor container and container information of the mobile terminal according to Embodiment 3.

DETAILED DESCRIPTION

Hereinafter, embodiments will be described in detail with reference to the drawings when necessary. However, excessively detailed descriptions will be omitted in some cases. For example, detailed descriptions of already well-known matters and repeated descriptions of substantially the same configurations will be omitted in some cases. This is for preventing the following description from being unnecessarily redundant, such that those skilled in the art can easily understand the description. It will be apparent to those skilled in the art from this disclosure that the following descriptions of the embodiments are provided for illustration only and not for the purpose of limiting the invention as defined by the appended claims and their equivalents.

Note that the inventor provides the attached drawings and the following description such that those skilled in the art can sufficiently understand the present disclosure, and does not intend to limit the subject recited in the scope of claims by the attached drawings and the following disclosure.

A description will now be given of the embodiments of the present invention applied to a sensor container for housing sensors for measuring a blood glucose level, for example.

Embodiment 1

Embodiment 1 will be described using FIGS. 1 to 10.

1-1 Sensor Container

Figure 1:
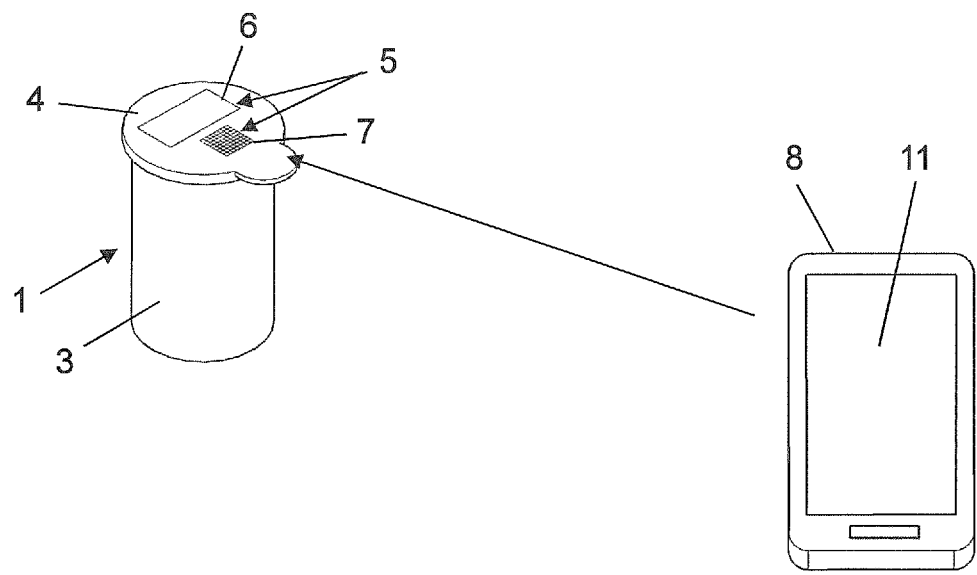
FIG. 1 is an external view of a sensor container according to Embodiment 1.

In FIG. 1, reference numeral 1 denotes a sensor container (an example of a sensor container). The sensor container 1 internally houses sensors 2 (an example of sensors) each having an elongated plate shape, for measuring a blood glucose level (an example of biological information). This sensor container 1 includes a cylindrical container body 3 (an example of a container body) having an opening portion on the upper face thereof, and a lid 4 (an example of a lid) that covers the opening portion of the container body 3 in an openable and closable manner.

Furthermore, the lid 4 is provided with a usable period mark indicating the usable period of the sensors 2 from the point in time when the lid 4 is released from the container body 3. Specifically, a display part 5 is provided on the lid 4, and this display part 5 includes a label 6 and a barcode 7 (an example of a mark). The label 6 displays, with characters, information regarding housed objects in the sensor container 1. The barcode 7 indicates sensor information (an example of sensor information, which is information regarding the sensors 2 in the container and represents the number of initially housed sensors 2, the usable period mark, etc.) regarding the sensors 2 housed in the container body 3, as shown in FIG. 7(a). That is to say, the sensor information is constituted by the barcode 7.

Note that two periods are set for the sensors 2 in the present embodiment. Namely, the usable period that is set by the aforementioned usable period mark and a validity period are set. The validity period indicates the period of time during which the measurement function of the sensors 2 operates validly, starting from the manufacture date of the sensors 2. Furthermore, the date obtained by adding the validity period to the manufacture date of the sensors 2 is deemed to be a validity expiration date. The validity expiration date is determined when the sensors 2 are manufactured.

The usable period indicates the period of time during which the measurement function of the sensors 2 operates validly, starting from a use start date, which is the date on which a sensor 2 is first taken out of an unused sensor container 1. The date obtained by adding the usable period to the use start date is deemed to be an expiration date. That is to say, such a usable period is set since the measurement function of the sensors 2 for measuring a blood glucose level deteriorates if the sensors 2 are exposed to the air for a long period of time, which is known well. Since the expiration date is determined when a sensor 2 is first taken out of an unused sensor container 1, the user needs to check the usable period (e.g., 90 days) of the sensors 2 when using an unused sensor container 1. For this reason, assuming that the usable period is 90 days, for example, a usable period mark that represents (sets) this usable period is constituted by the barcode 7, and is displayed on the display part 5.

Therefore, the user reads, as the sensor information, the number (e.g., 30) of initially housed sensors 2 and the usable period mark (e.g., 90 days) from the barcode 7, using a barcode reading unit (an example of a sensor information reading unit) 23 (see FIG. 6) of a mobile terminal (an example of a communication terminal) 8, as shown in FIG. 1. The mobile terminal 8 sets the usable period (e.g., 90 days) based on the usable period mark, and displays the read sensor information on a display unit 11 of the mobile terminal 8. With this display, the user can check the number of initially housed sensors 2 and the usable period. Thereafter, the mobile terminal 8 manages the number of sensors 2 in the sensor container 1 and the usable period of the sensors 2, based on the read sensor information.

Figure 4:
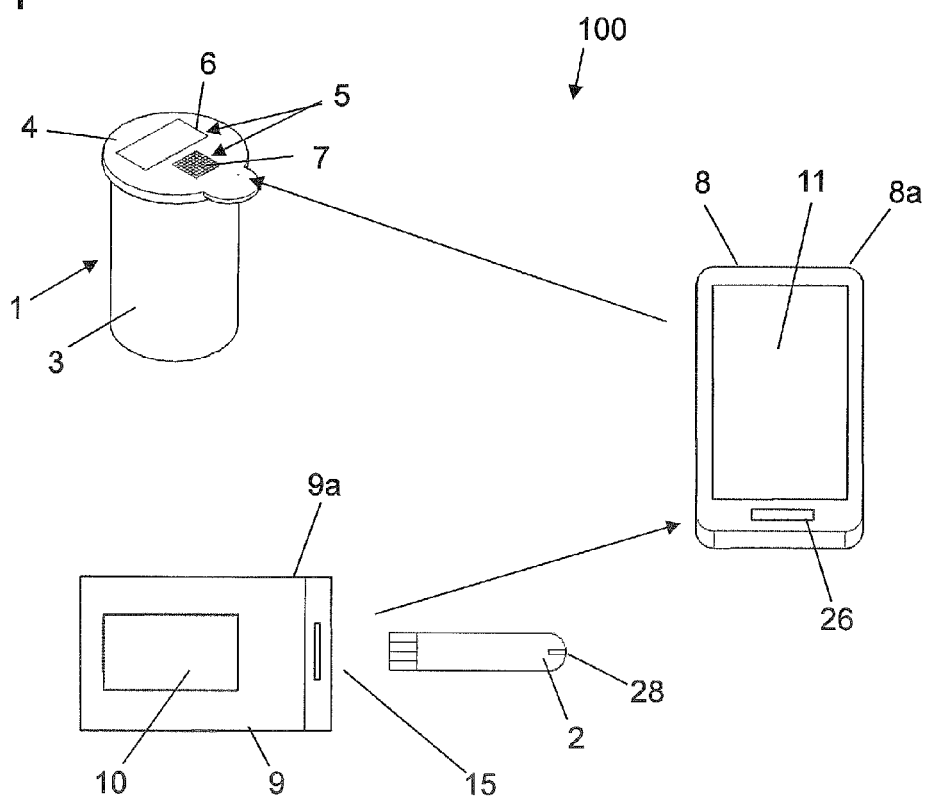
FIG. 4 is a diagram of a sensor information management system including the sensor container according to Embodiment 1.
Figure 8:
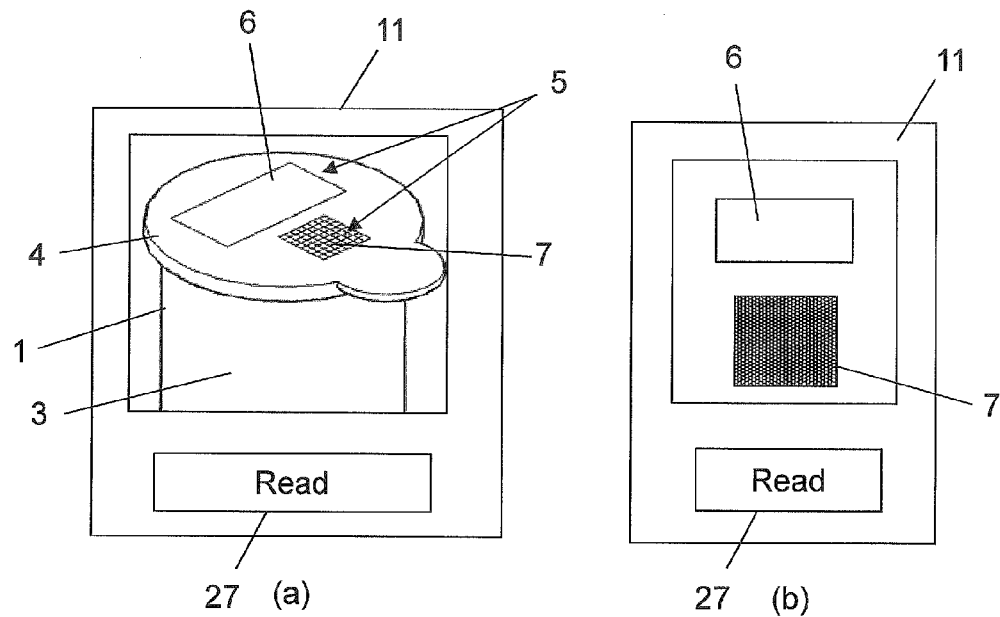
FIG. 8 is a diagram showing exemplary display by a display unit of the mobile terminal according to Embodiment 1.

When measuring a blood glucose level, the user takes a sensor 2 out of the sensor container 1, and upon the user attaching the sensor 2 to a blood glucose level measuring device (an example of a biological information measuring device) 9 as shown in FIG. 4, the measuring device 9 measures the blood glucose level. Next, the measuring device 9 transmits the measured blood glucose level to the mobile terminal 8. The mobile terminal 8, upon receiving the blood glucose level, decreases the number of sensors 2 that are currently managed, displays "Number of remaining sensors: 29" on the display unit 11, and manages the number of sensors 2 and the usable period thereof. This managing operation will be described later in detail. Note that communication between the measuring device 9 and the mobile terminal 8 may be wireless or wired communication.

Thereafter, upon the container body 3 being closed by the lid 4, the remaining sensors 2 are kept in the container body 3 in a sealed state, and the measurement function of the sensors 2 is prevented from deteriorating.

The basic configuration and operation in the present embodiment have been described thus far.

Figure 2:
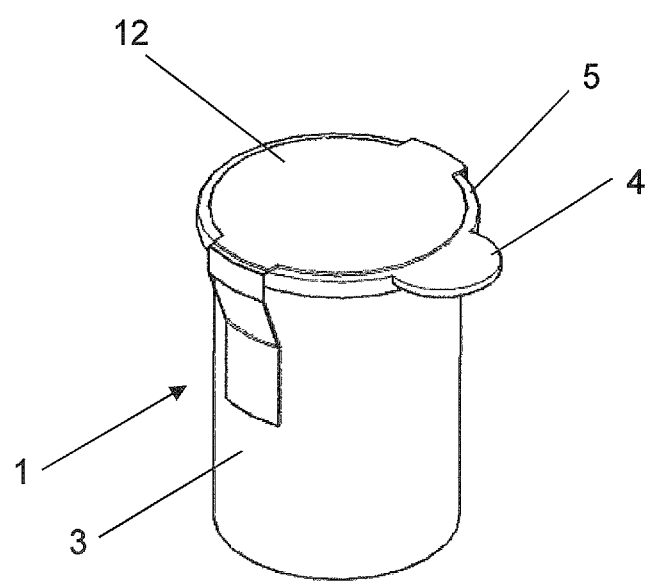
FIG. 2 is an external view of the sensor container to which a seal is attached according to Embodiment 1.

A feature of the sensor container 1 according to the present embodiment lies in that the number of initially housed sensors 2 and the usable period mark that sets the usable period of the sensors from the point in time when the lid 4 is released from the container body 3 are displayed only on the display part 5, and the display part 5 is covered with a seal 12 in a removable manner, as shown in FIG. 2.

Specifically, in an unused sensor container 1, the display part 5 in FIG. 1 is covered with the seal 12, and the number of initially housed sensors 2 and the usable period mark are hidden so as not to be visible from the outside. With this configuration, a state in which the user cannot be aware of the number of initially housed sensors 2 and the usable period mark is formed.

Furthermore, guidance display is provided on the surface of the seal 12 so as to prompt the seal 12 to be torn off the usable period mark (i.e., from above the display part 5) when the sensor container 1 begins to be used. Specifically, for example, a guidance such as "Tear off the seal and check the usable period" for prompting the user to tear off the seal 12 from the display part 5 is displayed with characters on the surface of the seal 12. For this reason, when an unused sensor container 1 is used, that is, when the lid 4 is first released from the container body 3, the user peels the seal 12 off the lid 4 and checks the usable period mark in accordance with the guidance regarding removal of the seal 12. Then, as shown in FIG. 1, the display part 5 is revealed from below the torn-off seal 12, and the sensor information (the number of initially housed sensors and the usable period mark) constituted by the barcode 7 is revealed. The label 6 on the display part 5 displays a guidance such as "Register the barcode", for example. Upon the user reading the sensor information from the barcode 7 using the barcode reading unit 23 (FIG. 6) of the mobile terminal 8, the mobile terminal 8 displays the read sensor information on the display unit 11 of the mobile terminal 8. With this display, the user can check the number of initially housed sensors 2 and the usable period based on the usable period mark. That is to say, with this usable period mark, the user can become aware of the usable period of the sensors for measuring a blood glucose level.

At this time, the sensor container 1 indicates that this sensor container 1 is in use, as a result of the seal 12 having been torn off, and can be distinguished from an unused sensor container 1 covered with the seal 12.

Figure 3:
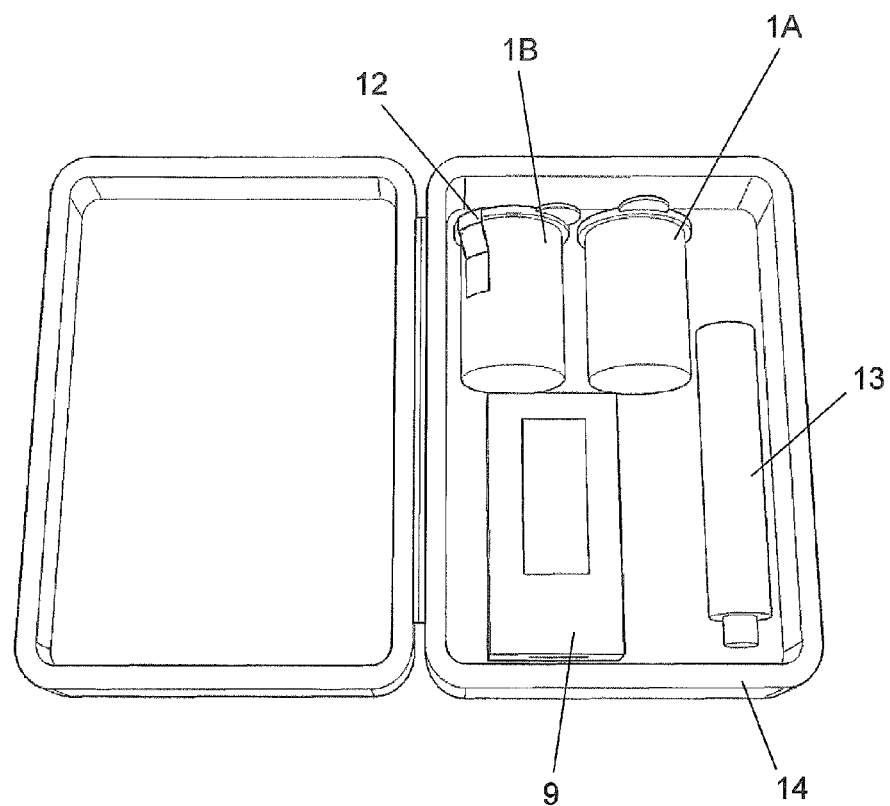
FIG. 3 is a perspective view showing a state in which the sensor container and a biological information measuring device are housed in a case according to Embodiment 1.

In a specific example, as shown in FIG. 3, a user often carries a spare sensor container 1B together with a sensor container 1A in use, the measuring device 9, and a puncture tool 13, in a housing case 14. In such a case, since the seal 12 of the sensor container 1A in use has been torn off, the sensor container 1A in use can be clearly distinguished from the unused sensor container 1B covered with the seal 12.

Accordingly, the user can take a sensor 2 that will expire sooner out of the sensor container 1A in use. Consequently, the sensors can be made more user-friendly.

Furthermore, the sensor container 1 in the present embodiment has a configuration in which the seal 12 is adhered so as to span from the container body 3 to the lid 4 in a state in which the container body 3 is closed by the lid 4, and a closed portion between the container body 3 and the lid 4 is sealed, as shown in FIG. 2. For this reason, in the case of using an unused sensor container 1, the seal 12 for sealing is reliably torn off when the lid 4 is released from the container body 3. Accordingly, the user can determine whether the sensor container 1 is in use or unused, and the sensors can be made more user-friendly.

Note that although the usable period mark is constituted by the barcode 7 on the display part 5 in the present embodiment, the usable period mark may be displayed as character information on the label 6 on the display part 5. With this configuration, when the user uses an unused sensor container 1, the user can visually read the usable period mark for the sensors 2 upon tearing off the seal 12 of the sensor container 1, and therefore the sensors are made more user-friendly.

Note that although the display part 5 for displaying the usable period mark is provided on the lid 4 in the present embodiment, the display part 5 may be provided on the outer surface of the container body 3 and hidden by the seal 12.

1-2 Sensor Information Management System

Since the sensors 2 housed in such a sensor container 1 are susceptible to light, the sensor container 1 is made of a light-blocking material. Accordingly, in a state in which the lid 4 of the sensor container 1 is closed, the state of the housed sensors 2 cannot be checked from the outside. In this situation, in order to check the accurate number of sensors in the sensor container 1, it is necessary to open the lid of the sensor container 1 and count the number of sensors every time, and the sensors are not user-friendly in this aspect.

Therefore, the present embodiment provides a sensor information management system in which the number of sensors 2 is managed such that the user can check the accurate number of sensors in the sensor container 1 without opening the lid 4. A detailed description will be given below.

FIG. 4 shows a sensor information management system 100 (an example of a sensor information management system) in the present embodiment. The sensor information management system 100 manages the number of sensors 2 housed in the sensor container 1 and the usable period of the sensors 2. The sensor information management system 100 includes the sensor container 1 that houses a plurality of sensors 2, the measuring device 9 on which a sensor 2 housed in the sensor container 1 is mounted when being used, and the mobile terminal 8 (an example of a communication terminal) to which a measured value obtained by the measuring device 9 is transmitted.

Note that the sensor container 1 is the same as one shown in FIG. 1.

1-2-1 Measuring Device

The measuring device 9 has a rectangular body case 9a and a sensor mount unit 15 provided on one end side of the body case 9a. Furthermore, the measuring device 9 includes a measurement unit 16 connected to the sensor mount unit 15, a control unit 17 connected to the measurement unit 16, and a communication unit 18 connected to the control unit 17, as shown in FIG. 5. Furthermore, a display unit 10, a battery cell 19, and a storage unit 20 are connected to the control unit 17.

1-2-2 Mobile Terminal

As shown in FIG. 4, the mobile terminal 8 has a rectangular body case 8a having the display unit 11. As shown in FIG. 6, the mobile terminal 8 has a communication unit 21 provided in the body case 8a, a control unit 22 connected to the communication unit 21, the barcode reading unit (an example of a sensor information reading unit) 23 connected to the control unit 22, a storage unit 24 connected to the control unit 22, and the like. The barcode reading unit 23 is constituted by a commonly-used barcode reader. The storage unit 24 stores the sensor information read by the barcode reading unit 23. Furthermore, the display unit 11, a battery cell 25, a power key 26, and a clock 30 are connected to the control unit 22.

As shown in FIG. 4, the display unit 11 of the mobile terminal 8 is provided over the almost whole area of the rectangular body case 8a, and enables touch input. Upon a button displayed on the display unit 11 by the control unit 22 being touched and selected by a finger of the user, a requested function is executed by the control unit 22 in accordance with the touch operation.

The control unit 22 of the mobile terminal 8 includes a processor such as a CPU, and realizes each function of the mobile terminal 8 by reading, executing, and processing a predetermined computer program. In particular, the control unit 22 acquires information indicating the number of initially housed sensors 2 in the sensor container 1 and the usable period mark from the information (FIG. 7(a)) read by the barcode reading unit 23, and causes the storage unit 24 to store the sensor information shown in FIG. 7(b). Then, the control unit 22 stores, in the storage unit 24, the information regarding the acquired usable period mark in FIG. 7(b) (i.e., the information regarding the usable period of the sensors 2 from the point in time when the lid 4 is released from the container body 3) and the information indicating the number of initially housed sensors 2 in the container body 3, and causes the display unit 11 of the mobile terminal 8 to display the information.

1-3 Operation of Sensor Information Management System

A description will now be given of a sensor management operation in the sensor container 1 with the above-described configuration.

1-3-1 Sensor Information Management

The user, when first using an unused sensor container 1, tears off the seal 12 so as to reveal the barcode 7 on the display part 5, as described above.

Next, upon the user turning on the power key 26 of the mobile terminal 8 and starting a predetermined application, a barcode reading screen is displayed on the display unit 11, as shown in FIG. 8(a). On this barcode reading screen, an image taken by the barcode reading unit 23 is displayed on the display unit 11. Accordingly, the user brings the barcode reading unit 23 close to the sensor container 1 such that the barcode 7 is displayed in an enlarged manner, as shown in FIG. 8(b).

In this state, upon the user touching and selecting a read button 27 displayed in the lower part of the display unit 11, the barcode reading unit 23 of the mobile terminal 8 in the present embodiment reads the information corresponding to the number (e.g., 30) of initially housed sensors 2 from the barcode 7, and transmits the read information to the control unit 22. The barcode reading unit 23 also reads the information corresponding to the usable period (e.g., 90 days) of the sensors 2 from the usable period mark, and transmits the read information to the control unit 22.

The control unit 22 then stores, in the storage unit 24, the number of initially housed sensors 2 as the number of sensors, and also stores, in the storage unit 24, the usable period based on the usable period mark, as shown in FIG. 7(b). Furthermore, the control unit 22 reads the current date from the clock 30 in FIG. 6, sets this date as the date when the lid 4 was first released from the container body 3 (i.e., the date when a sensor 2 is first taken out of the unused sensor container 1), and stores the date as the use start date of the sensors 2 (which will be referred to also as the use start date of the sensor container 1) in the storage unit 24.

Thereafter, the control unit 22 displays the number of sensors, the use start date of the sensors, and the usable period of the sensors on the display unit 11. For example, "The number of sensors is 30, the use start date of the sensors is Jan. 1, 2013, and the usable period of the sensors is 90 days" is displayed. The user who sees this display can become aware of the number of sensors, the use start date of the sensors 2, and the usable period of the sensors 2. Note that display of the usable period may be achieved by the control unit 22 calculating the actual expiration date and displaying the calculated expiration date (e.g., "The sensor usable period ends on Apr. 1, 2013").

Accordingly, the sensor information management system 100 in the present embodiment manages the number of sensors, and also manages the use start date and the usable period of the sensors 2. Thereafter, the mobile terminal 8 sets this sensor container 1 that is now in use as a container to be used, and manages the number of sensors 2 housed therein and the usable period of the sensors 2.

As described above, the usable period that is determined based on the date when a sensor 2 is first taken out of the sensor container 1 is set for the sensors 2. Accordingly, the user wants to use a sensor 2 taken out of the sensor container 1 in use when measuring a blood glucose level. In the present embodiment, since the seal 12 has been torn off the sensor container 1A in use as described above, the user can easily distinguish the sensor container 1A from the unused sensor container 1B. Accordingly, even if the user possesses a plurality of sensor containers, namely the sensor containers 1A and 1B as shown in FIG. 3, the user can select the sensor container 1A in use that will expire sooner and take a sensor 2 out of the sensor container 1A to measure a blood glucose level.

Thereafter, after the sensor 2 is attached to the sensor mount unit 15 of the measuring device 9 and blood is deposited on a deposit unit 28 of the sensor 2, the blood glucose level is measured by the measurement unit 16. The control unit 17 of the measuring device 9 displays the measured blood glucose level on the display unit 10, and wirelessly transmits the blood glucose level to the mobile terminal 8 via the communication unit 18. The operation at the time of blood glucose level measurement will now be described.

1-3-2 Blood Glucose Level Measurement

Figure 9:
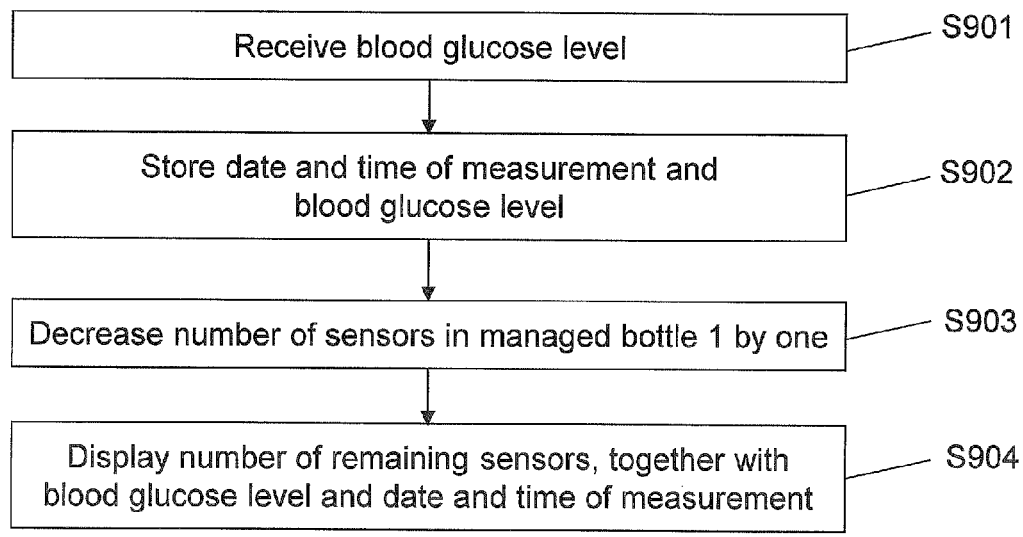
FIG. 9 is an operation flowchart of the mobile terminal according to Embodiment 1.

FIG. 9 shows an operation flowchart of the mobile terminal 8 at the time of blood glucose level measurement.

The control unit 22 of the mobile terminal 8 receives data of the measured blood glucose level from the measuring device 9 via the communication unit 21 (S901), and stores the received blood glucose level data in the storage unit 24 (S902).

The control unit 22 determines, due to reception of the blood glucose level data, that a sensor 2 has been taken out of the sensor container 1 and the blood glucose level has been measured. Therefore, the control unit 22 decreases the number of sensors 2 in the sensor container 1 stored in the storage unit 24 by one (S903).

At this time, the number of sensors 2 stored in the storage unit 24 is decreased by one and is set to 29.

Figure 10:
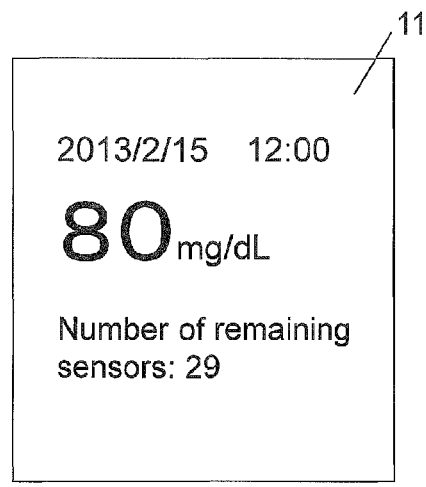
FIG. 10 is a diagram showing exemplary display by the display unit of the mobile terminal according to Embodiment 1.

Thereafter, the control unit 22 displays the number of remaining sensors, together with the received blood glucose level and the date and time of the measurement, on the display unit 11 of the mobile terminal 8, as shown in a "blood glucose level display screen" in FIG. 10 (S904).

FIG. 10 shows an exemplary "blood glucose level display screen" on the display unit 11 of the mobile terminal 8. In this exemplary display, the date and time of the measurement and the blood glucose level are displayed as <2013 Feb. 15 12:00 80 mg/dL> in the upper part of the display unit 11, and the number of sensors is displayed as "Number of remaining sensors: 29" in the middle part of the display unit 11.

Accordingly, the user can check the accurate number of remaining sensors 2 every time the user measures a blood glucose level, and consequently, the sensors 2 can be made more user-friendly.

Note that since there are cases where the sensor container 1 is used for a long period of time, the user may possibly forget the date when the user opened the sensor container 1 (the use start date of the sensors 2), and may no longer be aware of the expiration date of the sensors 2. Therefore, in the present embodiment, upon the user pressing a predetermined button (not shown) of the mobile terminal 8, the control unit 22 reads the number of sensors, the use start date of the sensors 2, and the usable period of the sensors 2 from the storage unit 24, and displays them on the display unit 11. For this reason, the user who sees this display can check the use start date of the sensors 2 and the usable period of the sensors 2, as well as the number of sensors. In this aspect as well, the sensors 2 are made more user-friendly.

1-4 Effects etc.

As described above, the sensor container 1 in the present embodiment is provided with the usable period mark indicating the usable period of the sensors 2 starting from the point in time when the lid 4 is released from the container body 3, on the container body 3 or the lid 4, and this usable period mark is covered with the removable seal 12. Accordingly, the user, upon tearing off the seal, can become aware of the usable period of the sensors for measuring a blood glucose level, due to the usable period mark. Furthermore, since the seal 12 of the sensor container 1A in use has been torn off, the sensor container 1A in use can be clearly distinguished from the unused sensor container 1B covered with the seal 12. Consequently, the sensors can be made more user-friendly.

Furthermore, in the sensor information management system 100 in the present embodiment, the number of initially housed sensors 2 (the number of sensors) that are housed in the sensor container 1 and the usable period mark are read from the display part 5 of the sensor container 1 by the barcode reading unit 23 of the mobile terminal 8, and are stored in the storage unit 24. Thereafter, for example, a blood glucose level is measured by the measuring device 9, and when the mobile terminal 8 receives the measured value, the number of sensors stored in the storage unit 24 is decreased and is displayed on the display unit 11 of the mobile terminal 8. For this reason, when a blood glucose level is measured by the measuring device 9 and this blood glucose level is sent to the mobile terminal 8, the mobile terminal 8 displays the accurate number of sensors in the sensor container 1 together with the blood glucose level, on the display unit 11. Consequently, the user can become aware of the accurate number of sensors every time the user measures a blood glucose level, and the sensors 2 are made more user-friendly in this aspect as well.

Thus far, in Embodiment 1, the system for managing the number of sensors 2 housed in one sensor container 1 and the usable period of the sensors 2 has been described.

Embodiment 2

2-1 Configuration

A sensor information management system 100 in the present embodiment uses individual identification information of a plurality of sensor containers, which is a main difference from the sensor information management system 100 in Embodiment 1 described above. Since the sensor container and the mobile terminal have the same configuration as that in Embodiment 1, the same reference numerals will be used and the same diagrams will be referred to.

Figure 11:
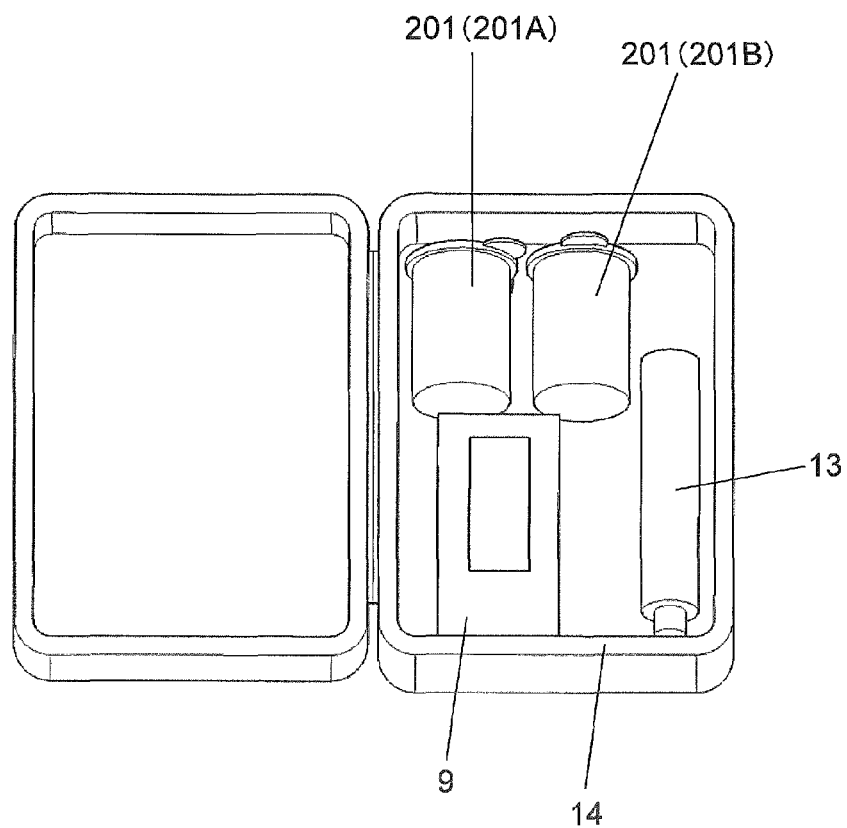
FIG. 11 is a perspective view showing a state in which a sensor container and a biological information measuring device are housed in a case according to Embodiment 2.

The user uses a housing case 14 such as the one shown in FIG. 11 for the purpose of daily blood glucose level measurement. A spare sensor container 201B is often put in the housing case 14, in addition to a sensor container 201A that is in use. In this case, for example, the user may possibly forget to return the sensor container 201A in use to the housing case 14 after measuring the blood glucose level at home, and then go out carrying this housing case 14. At this time, the user will open and use the spare sensor container 201B while away from home.

Therefore, Embodiment 2 expands the sensor information management system 100 in Embodiment 1 such that a plurality of sensor containers can be managed, and provides a system in which the number of sensors 2 housed in each sensor container is managed.

Specifically, the barcode 7 provided on each sensor container 201 in the present embodiment has individual identification information of the sensor container 201, as shown in FIG. 12(a). That is to say, this individual identification information, as well as the number of initially housed sensors 2 (number of sensors) housed in this sensor container 201, and the usable period mark that sets the usable period of the sensors 2 from the point in time when the lid 4 is released from the sensor container 201, are constituted by the barcode 7.

The sensor information management system 100 in the present embodiment includes container information (an example of sensor information) that indicates information regarding the sensor container 201. As shown in FIG. 12(b), this container information has the individual identification information of the respective sensor containers 201A and 201B, the number of sensors representing the number of remaining sensors 2 in the sensor containers 201, a bottle use start date (which will be referred to also as the use start date of the sensors) representing the use start date of the sensor containers 201, and the usable period of the sensors 2.

2-2 Operation

The operation of the sensor information management system 100 according to the present embodiment will now be described in accordance with an operation flowchart in FIG. 13. Here, a description will be given using an exemplary case where the user has left the sensor container 201A in use at home and uses the spare sensor container 201B while away from home.

2-2-1 Processing for Adding Container Information

Figure 14:
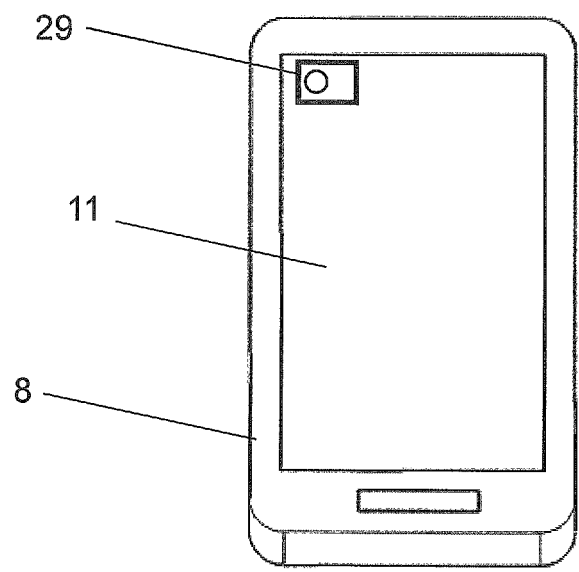
FIG. 14 is a perspective view of the mobile terminal according to Embodiment 2.

Initially, the user selects, by means of a touch operation, a bottle select icon 29, which is displayed on the display unit 11 of the mobile terminal 8 as shown in FIG. 14 (S1301). Then, as shown in exemplary display of a "top screen" in FIG. 15, the control unit 22 of the mobile terminal 8 causes the display unit 11 to display the top screen for prompting the user to check the sensor container (which will be referred to also as a "bottle") (S1302).

Figure 15:
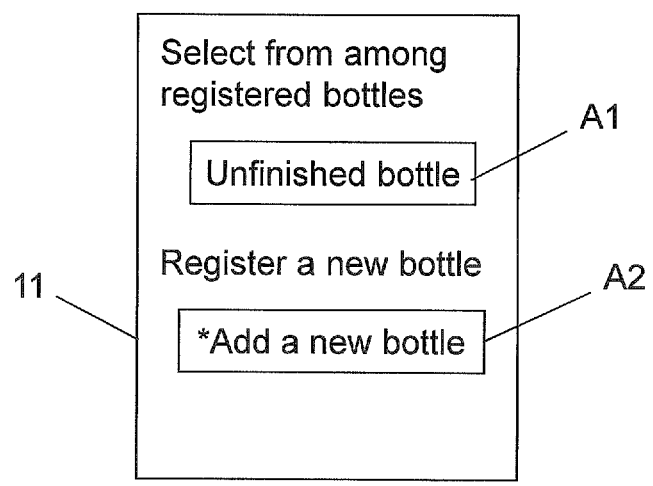
FIG. 15 is a diagram showing exemplary display by a display unit of the mobile terminal according to Embodiment 2.

As shown in FIG. 15, the mobile terminal 8 in the present embodiment is provided with an "*Add a new bottle" button A2, which is an example of a displayed execution operation unit, on the top screen of the mobile terminal 8. Upon the user selecting this "*Add a new bottle" button A2 (S1303), the control unit 22 activates the barcode reading unit 23 (S1304). At this time, the display unit 11 displays the barcode reading screen, as in FIGS. 8(a) and 8(b). The user tears off the seal 12 of the sensor container 201B to reveal the display part 5. Then, the container information is acquired by the barcode 7 on the display part 5 of the sensor container 201B being read by the barcode reading unit 23. The container information contains three pieces of information, namely the individual identification information of the sensor container 201B, the number of initially housed sensors 2 (number of sensors), and the usable period of the sensors 2 based on the usable period mark.

The control unit 22 compares the individual identification information in the acquired container information with the individual identification information in the container information that is already stored in the storage unit 24 (S1305). If the result of this comparison is that the acquired container information is not yet stored in the storage unit 24, the control unit 22 acquires the current date from the clock 30 in FIG. 5, and adds new container information ("201B" in FIG. 12(b)) with the acquired date as the bottle use start date. That is to say, the control unit 22 determines the day when a sensor 2 is first taken out of the sensor container 201B to be the use start date (bottle use start date) of the sensor container 201B, and adds this date to the container information.

Accordingly, as shown in FIG. 12(b), the newly acquired container information contains four pieces of information, namely the individual identification information of the sensor container 201B, the number of sensors 2 (which is the same as the number of initially housed sensors 2 here), the bottle use start date, and the usable period of the sensors 2. Then, the control unit 22 stores the added container information in the storage unit 24 (FIG. 6) (S1306).

Figure 16:
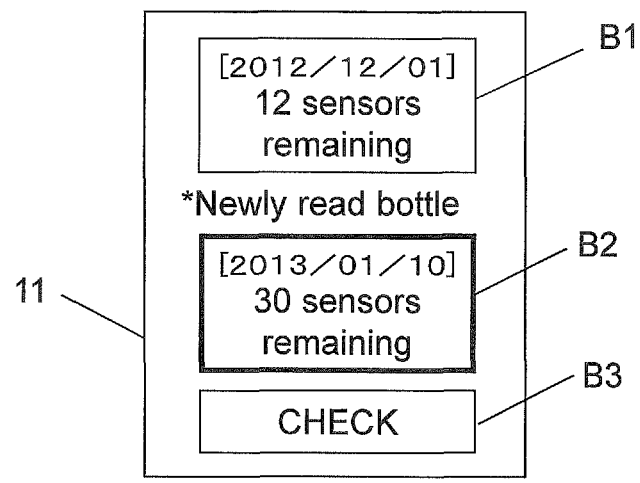
FIG. 16 is a diagram showing exemplary display by the display unit of the mobile terminal according to Embodiment 2.

Next, the control unit 22 causes the display unit 11 to display a bottle check screen, as shown in the exemplary display in FIG. 16 (S1307). On this screen, the number of initially housed sensors 2 (number of sensors) in the sensor container 201B and the use start date thereof are displayed as a container information button B2 on the display unit 11. Specifically, the container information button B2 indicating the newly acquired container information of the sensor container 201B is displayed together with the characters <[2013 Jan. 10] 30 sensors remaining> representing the bottle use start date and the number of sensors, in the middle part of the display unit 11.

As a result of this processing, if the new sensor container 201B is added in the sensor information management system 100, the container information (the number of sensors and the bottle use start date) thereof is displayed as the container information button on the display unit 11. Accordingly, the sensors 2 are made more user-friendly for the user.

Furthermore, the control unit 22 reads all container information from the storage unit 24, and displays the read container information as container information buttons together with characters indicating the bottle use start date and the number of sensors.

Specifically, two container information buttons B1 and B2 respectively for the sensor container 201A and the sensor container 201B are displayed. In the upper part of the display unit 11, the container information button B1 representing the container information of the sensor container 201A is displayed together with the characters <[2012 Dec. 1] 12 sensors remaining> indicating the bottle use start date and the number of sensors.

For this reason, since the container information of not only the sensor container 1B that is read at this time but also other sensor containers is displayed, the managed container information can be checked simultaneously.

Moreover, here, the control unit 22 displays the container information button B2 based on the newly added new container information that is read by the barcode reading unit 23 at this time, in an emphasized manner by enclosing it with a bold frame, as shown in FIG. 16, together with the characters "*Newly read bottle" (this display will be hereinafter referred to as "specific display"). For this reason, the user can easily recognize the number of sensors in the sensor container 201B that is newly added at this time and the bottle use start date thereof.

Figure 17:
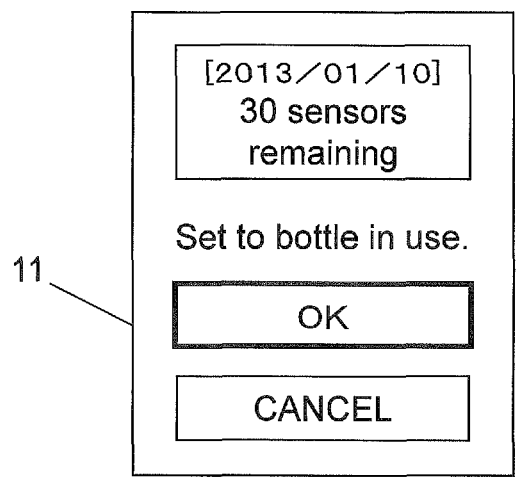
FIG. 17 is a diagram showing exemplary display by the display unit of the mobile terminal according to Embodiment 2.

Upon the newly registered container information button B2 being touched and selected by the user on the bottle check screen in FIG. 16, the control unit 22 causes the display unit 11 to display a screen for confirming that the selected bottle will be set as the bottle in use, as shown in FIG. 17. Upon the user checking the number of sensors and the bottle use start date indicated by the container information button displayed in the upper part of the screen and selecting an "OK button" in the middle part of the check screen (S1308), the control unit 22 sets the newly registered sensor container 201B as the container to be used (bottle in use) (S1313).

As a result of executing the above operation, even in the case where the user has left the sensor container 201A in use at home and has no choice but to use the spare sensor container 201B while away from home, the user can use the sensor container 201B after setting the sensor container 201B as a new container to be used, in addition to the sensor container 201A.

The user performs blood glucose level measuring processing shown in FIG. 9, using a sensor 2 taken out of the sensor container 201B. After the measurement, the control unit 22 updates the number of sensors (i.e., decreases the number of sensors by one) in the container information of the sensor container 201B, which is the container to be used.

2-2-2 Check and Change of Container Information

Then, after the user goes back home and returns the sensor container 201A to the housing case 14, the sensor container 201A and the sensor container 201B are housed again in the housing case 14, as shown in FIG. 11. The user wants to use the sensor container 201A with the earlier use start date, but both the sensor containers 201A and 201B are in an opened state, and therefore the user cannot tell which one is the sensor container 201A and which one is the sensor container 201B.

Therefore, in the present embodiment, the container information of the sensor container 201A or 201B is read by the barcode reading unit 23, and the sensor container with the earlier use start date (i.e., the sensor container 201A) is thereby identified out of the sensor containers 201A and 201B.

The procedure for this will be described below in accordance with an operation flowchart in FIG. 13.

Upon the user selecting the bottle select icon 29 in FIG. 14 displayed on the display unit 11 of the mobile terminal 8 (S1301), the top screen in FIG. 15 is displayed (S1302). The top screen of the mobile terminal 8 in the present embodiment is provided with an "Unfinished bottle" button (an example of the displayed execution operation unit) A1 as well as the "*Add a new bottle" button A2, as shown in FIG. 15. The "Unfinished bottle" button A1 is for displaying information regarding the sensor containers whose container information has already been acquired and stored in the storage unit 24.

Figure 18:
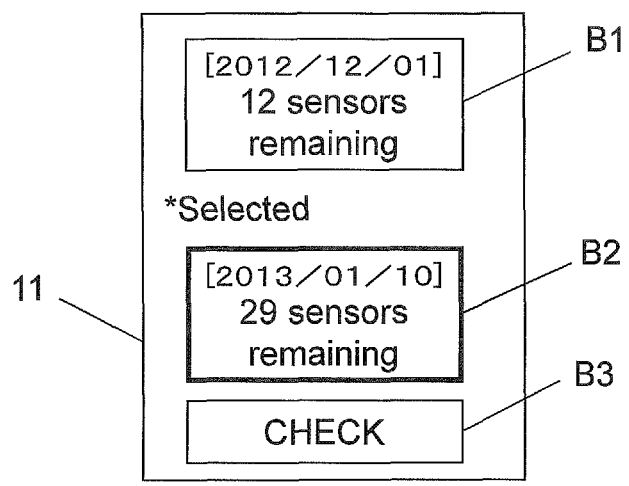
FIG. 18 is a diagram showing exemplary display by the display unit of the mobile terminal according to Embodiment 2.

If the user selects the "Unfinished bottle" button A1 (S1303), the control unit 22 reads all container information from the storage unit 24, and displays a bottle check screen in FIG. 18 on the display unit 11 (S1309). On this screen, each piece of the read container information is displayed as the container information button, together with characters indicating the bottle use start date and the number of sensors.

Specifically, two container information buttons B1 and B2 respectively for the sensor container 201A and the sensor container 201B are displayed. In the upper part of the display unit 11, the container information button B1 representing the container information of the sensor container 201A is displayed together with the characters <[2012 Dec. 1] 12 sensors remaining> indicating the bottle use start date and the number of sensors. That is to say, since the container information of not only the sensor container 201B that is newly acquired at this time but also other sensor containers is displayed, the user can check all the managed container information at a time.

Furthermore, when the control unit 22 displays the container information (the number of sensors in the container body 3 and the bottle use start date thereof) on the display unit 11, the control unit 22 displays the container information in ascending order of the use start date of the sensors 2. Specifically, a configuration in which the container information is displayed in ascending order of the bottle use start date (in order of the use start date) from the top of the display unit 11 is employed. For this reason, since the container information button B2 for the sensor container 201B that is added at this time is specifically displayed at the bottom, the newly added container information can be easily identified.

Note that the order on the display unit 11 is not limited to the aforementioned order, and the control unit 22 may display the container information in descending order of bottle use start date from the top of the display unit 11.

Furthermore, as shown in FIG. 18, the sensor container 201B that is currently set as the container to be used is enclosed with a bold frame and is specifically displayed together with the characters "*Selected". Note that since the user has used the sensor container 201B while away from home to perform measurement once, the container information button B2 displays the number of sensors 2 as "29", together with the use start date of the sensors 2.

This bottle select screen displays, as an example of an operation key for identifying each sensor container 201, a bottle check button B3 for reactivating the barcode reading unit 23, together with the characters "CHECK", in the lower part of the display unit 11.

Figure 19:
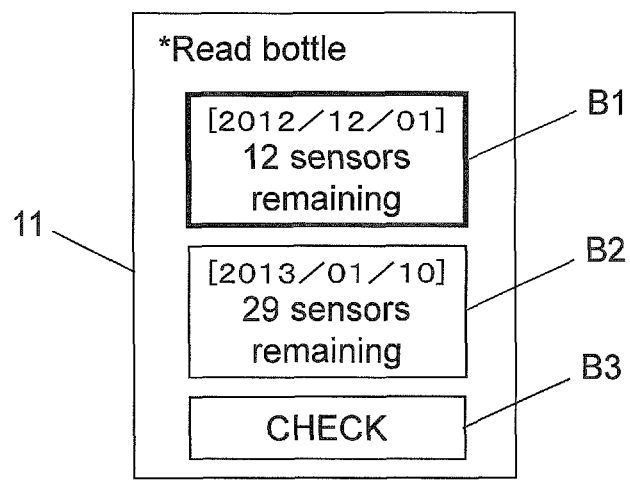
FIG. 19 is a diagram showing exemplary display by the display unit of the mobile terminal according to Embodiment 2.

If the selected bottle (i.e., the specifically displayed bottle) is different from the bottle that the user wants to use, the user selects the check button B3 ("No" in S1310). Then, the control unit 22 of the mobile terminal 8 in the present embodiment activates the barcode reading unit 23 in response to the operation on the check button B3, and upon reading the container information from the display part 5 of the sensor container 201 using the barcode reading unit 23 (S1304), the control unit 22 detects the container information corresponding to the acquired individual identification information of the sensor container 201 from among the container information stored in the storage unit 24 (S1305). Then, the control unit 22 specifically displays the number of sensors and the use start date in the detected container information on the display unit 11 (displays in a state of being enclosed with a bold frame), as shown in FIG. 19 (S1311). Here, the control unit 22 has read the barcode information of the sensor container 201A and acquired the container information of the sensor container 201A from the storage unit 24. At this time, as shown in FIG. 19, the container information button B1 for the sensor container 201A is specifically displayed in a state of being enclosed with a bold frame, and is displayed together with the characters "*Read bottle" at the top of the display unit 11.

Furthermore, as shown in FIG. 19, the control unit 22 reads other container information stored in the storage unit 24, and displays, on the display unit 11, the number of sensors and the use start date corresponding to the individual identification information in the container information of each container. That is to say, the control unit 22 reads all container information from the storage unit 24 and, as shown in a bottle check screen in FIG. 19, the control unit 22 displays, as container information buttons, the container information together with characters indicating the bottle use start date and the number of sensors, on the display unit 11.

At this time, since the control unit 22 displays the container information in ascending order of the use start date of the sensors (bottle use start date) from the top of the display unit 11, the user can recognize that "the container that has just been read is the sensor container with the earliest use start date of the sensors", due to the specific display with a bold frame and the display position thereof.

Furthermore, the bottle use start date is determined when a new sensor container 201 is used. For this reason, although the user may possibly forget this bottle use start date in the case of using the sensor container 201 for a long period of time, in the present embodiment, once the container information of the sensor container 201 is read by the barcode reading unit 23, the read container information is stored in the storage unit 24 and displayed as the container information button on the display unit 11. Furthermore, the bottle use start date is displayed together with the number of sensors on the displayed container information button. For this reason, the user can check the bottle use start date, which is likely to be forgotten, using the mobile terminal 8 that the user usually uses, and therefore the sensors 2 are made more user-friendly in this aspect as well.

Figure 20:
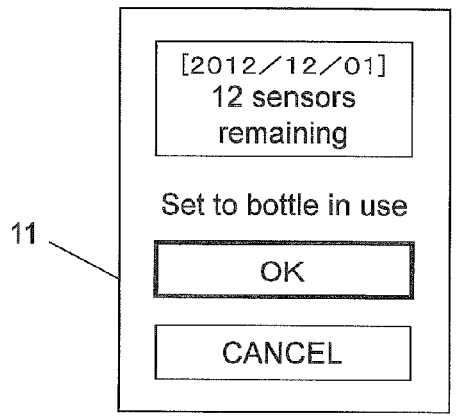
FIG. 20 is a diagram showing exemplary display by the display unit of the mobile terminal according to Embodiment 2.

Thereafter, upon this container information button B1 being touched and selected by the user, the control unit 22 displays a container information check screen, as shown in a bottle select screen in FIG. 20 (S1312). Upon the user checking the container information button and selecting an "OK button" in the middle part of the check screen, the control unit 22 sets the sensor container 201A as the container to be used (S1313).

Note that the control unit 22 of the mobile terminal 8 in the present embodiment activates the barcode reading unit 23 in response to an operation on the displayed execution operation units (the "Unfinished bottle" button A1 and the aforementioned "*Add a new bottle" button A2) in FIG. 15. In order to read the display part 5 of the sensor container 201 using this barcode reading unit 23 and display the acquired container information of each sensor container 201 together with display of the number of sensors on the display unit 11, the control unit 22 causes the display unit 11 to display the operation key (the check button B3) for reactivating the barcode reading unit 23.

Upon the check button B3 being selected on the bottle check screen in FIG. 16, 18, or 19, the container information can be read from the other sensor container 201 using the barcode reading unit 23.

Note that if a "Cancel button" in the lower part of the check screen in FIG. 17 (S1308) or FIG. 20 (S1312) is selected, the screen returns to FIG. 16 (S1307) or FIG. 19 (S1311), respectively. The user can also directly select the container information buttons B1 and B2 displayed on the bottle check screen in FIGS. 16, 18, and 19.

When the read container information pertains to the sensor container 201B, the container information button B2 displayed second from the top on the bottle check screen in FIG. 19 is specifically displayed by being enclosed with a bold frame. The user can recognize that "there is a sensor container with earlier use start date than the use start date of the container that has just been read", due to the specific display with a bold frame and the display position thereof. Consequently, the sensors 2 are made more user-friendly.

Thus, the sensor information management system 100 in the present embodiment can manage the number of sensors in each of a plurality of sensor containers (in this example, the sensor container 201A and the sensor container 201B) and the usable period of the sensors, and the user can check them with the display of the mobile terminal 8. Accordingly, the sensors 2 are made more user-friendly.

In the present embodiment, the individual identification information of each sensor container 201 is read by the barcode reading unit 23 of the mobile terminal 8, the read individual identification information is stored in the storage unit 24, and the number of sensors and the use start date are managed. That is to say, the sensor containers 201 do not need to have a configuration for managing the number of sensors and the usable period by themselves (e.g., each sensor container 201 does not need to visibly display the container information on the display part 5 thereof), and therefore the configuration of the sensor containers 201, which are to be discarded after use, can be simplified.

Note that the container to be used is the container whose number of sensors 2 is to be decreased by one when the user measures a blood glucose level. Accordingly, after the user measures a blood glucose level using the measuring device 9 and the measuring device 9 transmits the blood glucose level to the mobile terminal 8, the mobile terminal 8 extracts the container information of the container to be used (the sensor container 201) from a container information group in the storage unit 24, based on the individual identification information, and decreases the number of sensors held in the extracted container information. Thereafter, the number of sensors stored in the storage unit 24 is updated.

As described above, in the sensor information management system 100 in the present embodiment, the container information of the sensor container 201B as well as the container information of the sensor container 201A are read by the barcode reading unit 23, and the sensor container 201B is then registered under the management of the mobile terminal 8 and can be added as the container to be used. Consequently, the sensors 2 housed in a plurality of sensor containers can be managed.

Note that the control unit 22 of the mobile terminal 8 in the present embodiment may display a notice based on the expiration date that is set by the usable period mark. Specifically, the control unit 22 reads today's date from the clock 30, and checks that today's date is smaller than the expiration date of the sensors 2. This checking is performed when the number of sensors is displayed on the display unit 11, for example. If the expiration date of the sensors 2 is approaching, for example, if it is 10 days before the expiration date, the control unit 22 displays a notice (not shown) indicating that the expiration date is approaching, together with display of the number of sensors, on the display unit 11. With this configuration, since the notice is displayed on the display unit 11 if the expiration date of the sensors 2 is approaching, the user can become aware that the expiration date of the sensors 2 is approaching, and the sensors 2 can be made more user-friendly in this aspect as well.

2-3 Effects Etc

As described above, with the sensor information management system 100 in the present embodiment, in addition to the effects of Embodiment 1, the individual identification information of each sensor container 201 and the information indicating the number of initially housed sensors 2 (number of sensors) housed in each sensor container 201 and the usable period mark are read from the barcodes 7 of a plurality of sensor containers 201, using the barcode reading unit 23 of the mobile terminal 8, and are stored in the storage unit 24 for each sensor container 201. Consequently, the sensors 2 housed in the plurality of sensor containers 201 can be managed collectively.

Furthermore, even if there are a plurality of sensor containers 201 that are in use and the usable periods thereof are different, the container information is displayed in order of the expiration date. Accordingly, the user can efficiently use the sensors in the sensor containers 201, and the sensors are made more user-friendly in this aspect as well.

Embodiment 3

3-1 Configuration

A sensor information management system 100 in the present embodiment uses, as the container information, the validity expiration date based on the manufacture date, which is a main difference from Embodiment 2 described above. Since the sensor container and the mobile terminal have the same configuration as that in Embodiment 1, the same reference numerals will be used and the same diagrams will be referred to.

The operation of the sensor information management system 100 according to the present embodiment will now be described with focus on differences from Embodiment 2.

3-2 Operation

Figures 12, 13:
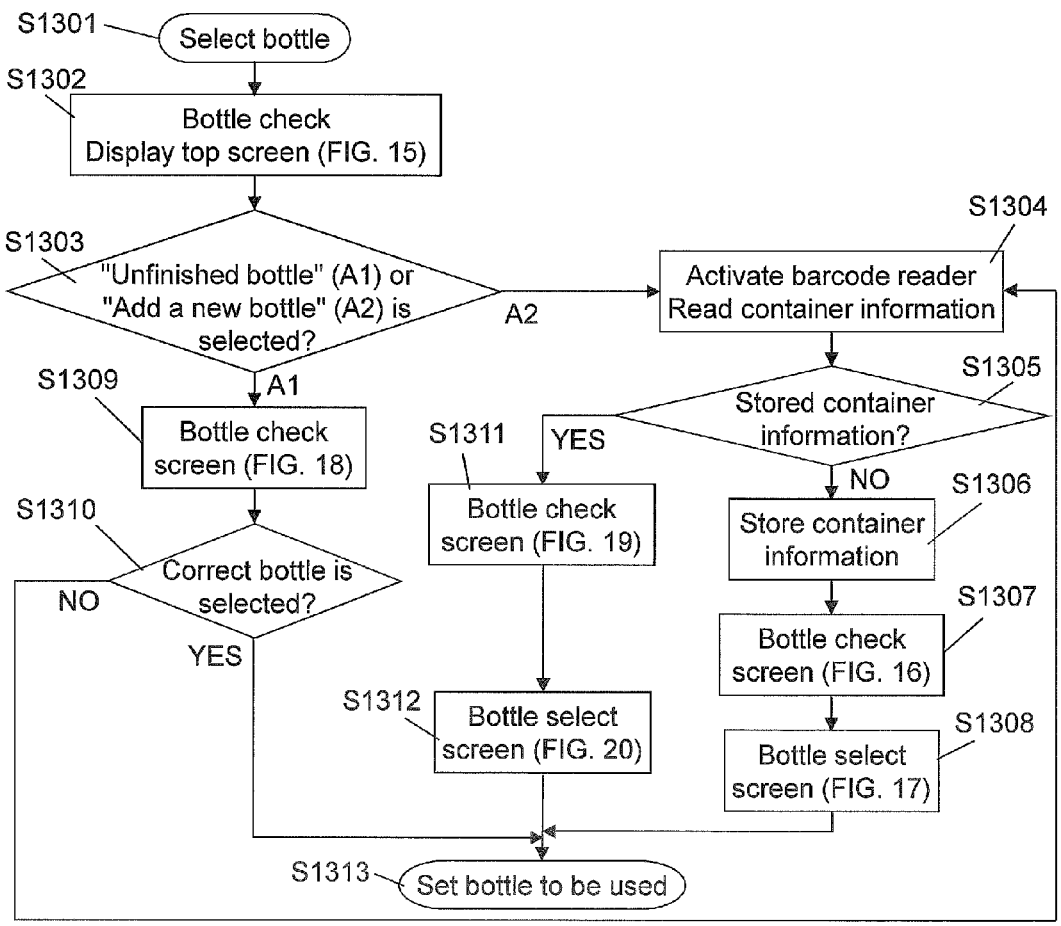
FIG. 12 is a diagram showing the content of barcode information of the sensor container and container information of a mobile terminal according to Embodiment 2.
FIG. 13 is an operation flowchart of the mobile terminal according to Embodiment 2.

In Embodiment 2, the read bottle check screen (FIGS. 16, 18, and 19) displayed in step S1307 in FIG. 13 displays the container information in ascending order of the bottle use start date (in order of the use start date) from the top of the display unit 11. In Embodiment 3, the container information is displayed in ascending order of the manufacture date of the sensors 2 (in order of the manufacture date) from the top of the display unit 11. That is to say, as mentioned above, some sensors 2 are provided with a validity expiration date based on their manufacture date (e.g., the manufacture date+15 months), and in this case, the container information is displayed in order of the manufacture date of the sensors 2. Thus, the sensor container 201 that houses the sensors 2 with the earlier manufacture date can be easily checked, and the sensors 2 are made more user-friendly.

The operation of the sensor information management system 100 according to the present embodiment will now be described.

First, the container information in the present embodiment is stored in the storage unit 24, and contains the manufacture date and the validity expiration date of the sensors 2 housed in the sensor containers 201A and 201B, in addition to the number of sensors 2, the usable period, the individual identification information, and the bottle use start date regarding each of the sensor containers 201A and 201B, as shown in FIG. 22(*b*). The manufacture date and the validity expiration date of the sensors 2 are acquired by information contained in the barcode 7 of the sensor containers shown in FIG. 22(*a*) being read using the barcode reading unit 23 (FIG. 6) of the mobile terminal 8.

Figure 21:
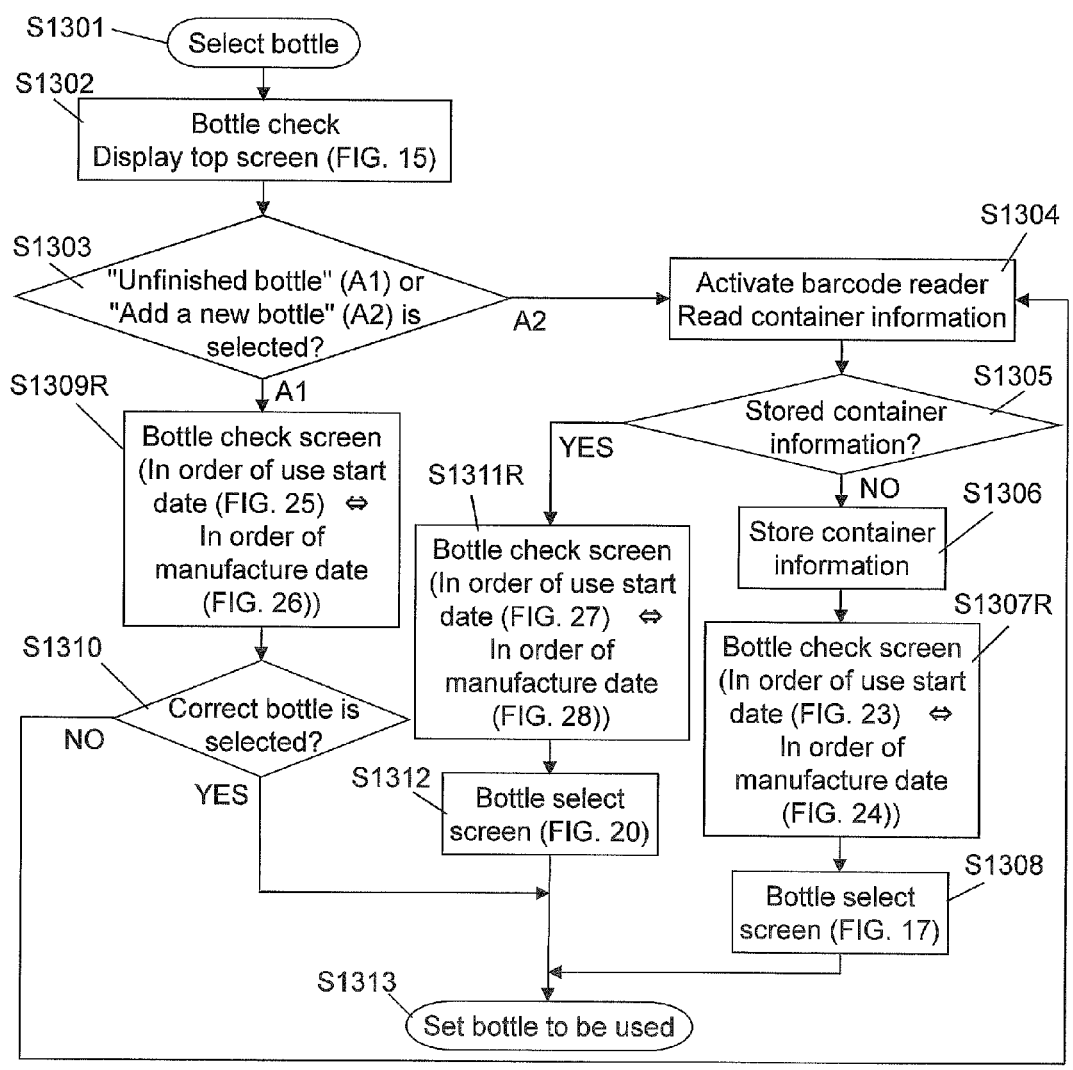
FIG. 21 is an operation flowchart of a mobile terminal according to Embodiment 3.

FIG. 21 is an operation flowchart of the mobile terminal 8 in the present embodiment. Here, the operation in step S1307R is performed in place of the operation in step S1307 in FIG. 13 in Embodiment 2, the operation in step S1309R is performed in place of the operation in step S1309 in FIG. 13, and the operation in step S1311R is performed in place of the operation in step S1311 in FIG. 13.

Figure 23:
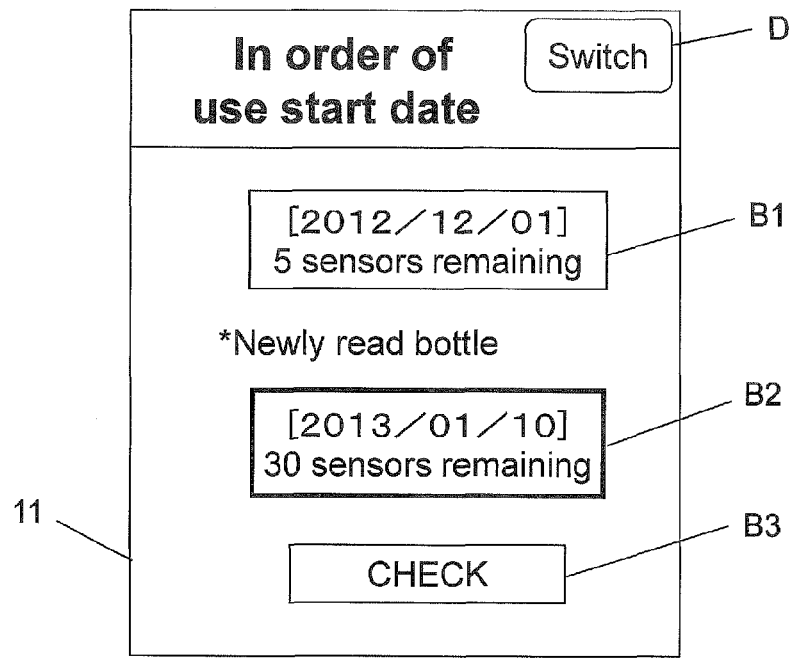
FIG. 23 is a diagram showing exemplary display by a display unit of the mobile terminal according to Embodiment 3.
Figure 24:
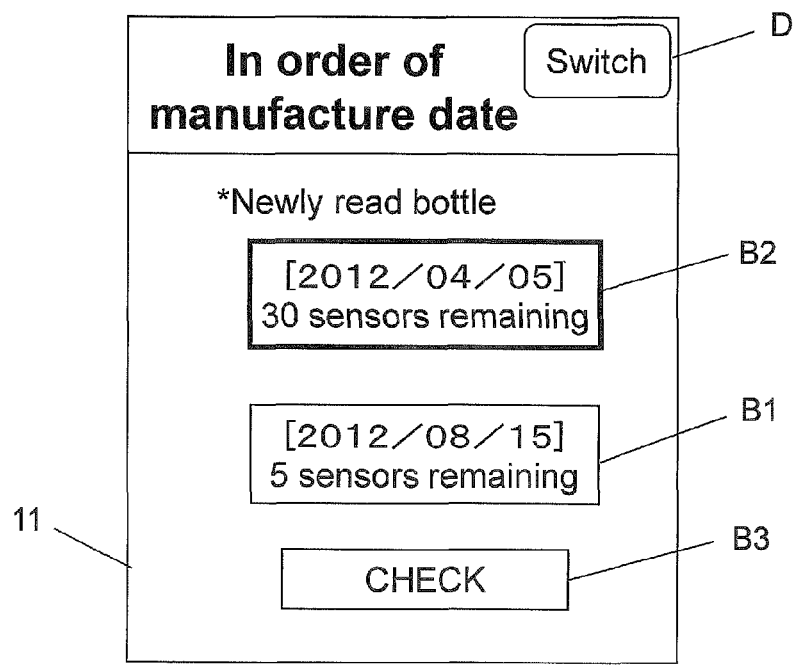
FIG. 24 is a diagram showing exemplary display by the display unit of the mobile terminal according to Embodiment 3.

FIGS. 23 and 24 are bottle check screens at the time of adding a new sensor container 201 as a container to be managed, and correspond to FIG. 16 in Embodiment 2.

A specific operation will now be described. In step S1307R in FIG. 21, the control unit 22 displays a bottle check screen in FIG. 23. At this time, as mentioned above, the control unit 22 initially reads the container information of each sensor container stored in the storage unit 24, and displays the read container information in order of earliest bottle use start date (in order of the use start date) from the top of the display unit 11. In addition, a switching button (an example of the operation key) D for displaying the container information in ascending order of the manufacture date of the sensors 2 (in order of the manufacture date) is displayed at the upper right of the display unit 11.

Note that the control unit 22 may display the container information in descending order of the bottle use start date from the top of the display unit 11. Regarding the order of the manufacture date as well, the control unit 22 may display the container information in descending order of the manufacture date of the sensors from the top of the display unit 11.

Upon the user touching and selecting this switching button D, the control unit 22 detects the manufacture date of the sensors 2 in the container information (FIG. 22(*b*)) stored in the storage unit 24. The control unit 22 then displays the container information in ascending order of the manufacture date of the sensors 2 from the top of the display unit 11, as shown in FIG. 24. When the container information is displayed in order of the manufacture date, the manufacture date of the sensors 2 is displayed in the container information buttons B1 and B2, in place of the use start date of the sensors 2.

Consequently, the user can easily identifies the sensor container 201B that houses the sensors 2 with the earlier manufacture date, and the sensors 2 are made more user-friendly.

Also, when the container information is displayed in order of the manufacture date, the switching button D is provided at the upper right of the screen, and accordingly the user can easily switch between the display in order of the use start date and the display in order of the manufacture date by means of a touch operation, and the sensors 2 are made more user-friendly in this aspect as well.

Figure 25:
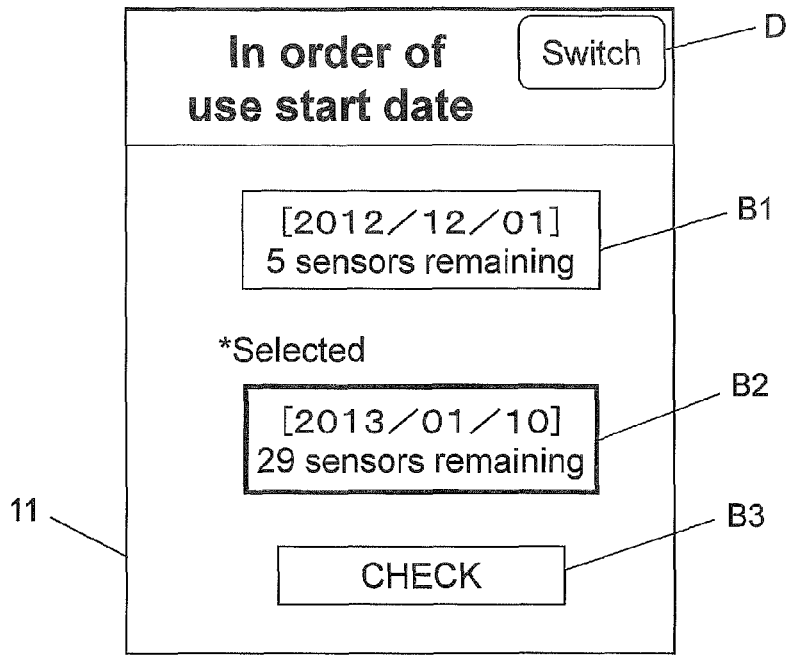
FIG. 25 is a diagram showing exemplary display by the display unit of the mobile terminal according to Embodiment 3.
Figure 26:
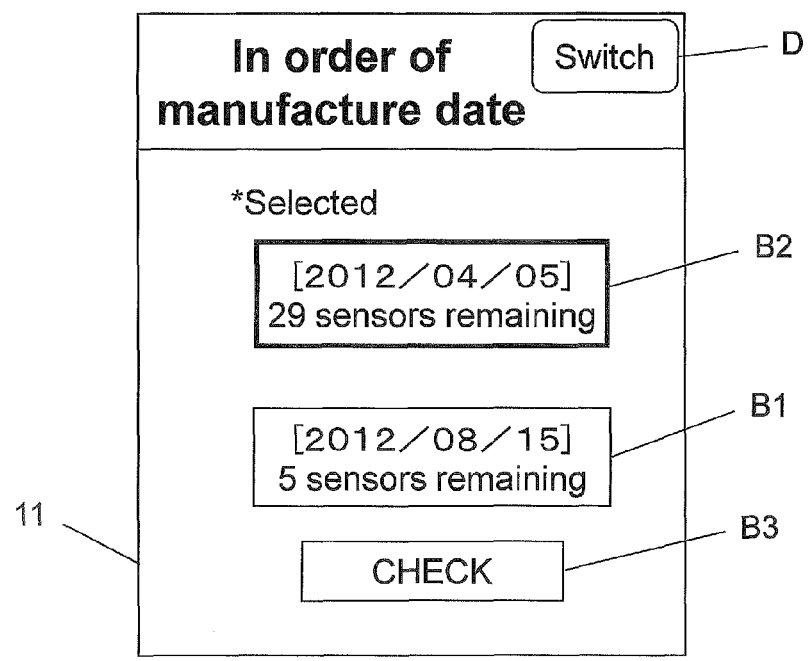
FIG. 26 is a diagram showing exemplary display by the display unit of the mobile terminal according to Embodiment 3.

In step S1309R in FIG. 21, the control unit 22 causes the display unit 11 to display a bottle check screen in FIG. 25 or 26. FIGS. 25 and 26 are screens at the time of checking the sensor container 201 that is currently the container to be used, and correspond to FIG. 18 in Embodiment 2. Since the display of the display unit 11 in FIGS. 25 and 26 is also provided with the switching button D at the upper right of the screen, the control unit 22 can easily switch between the display in order of the use start date in FIG. 25 and the display in order of the manufacture date in FIG. 26.

Figure 27:
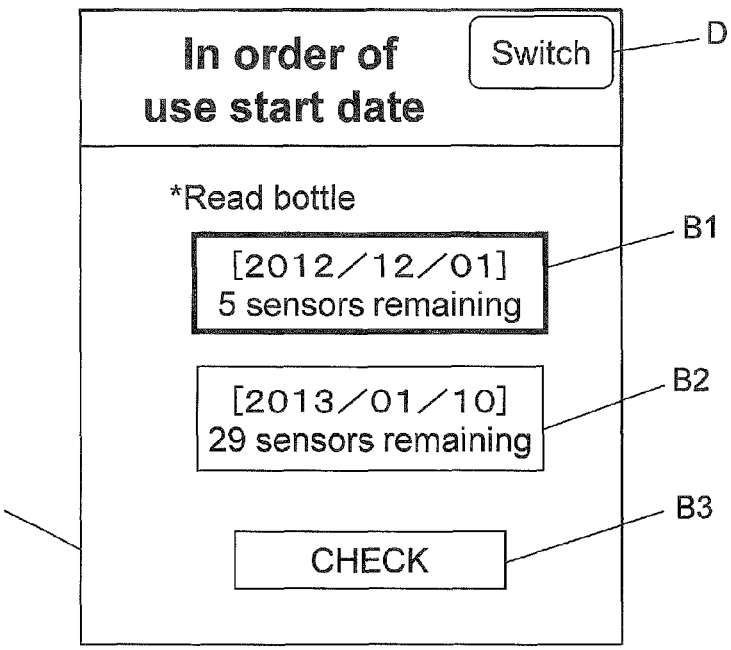
FIG. 27 is a diagram showing exemplary display by the display unit of the mobile terminal according to Embodiment 3.
Figure 28:
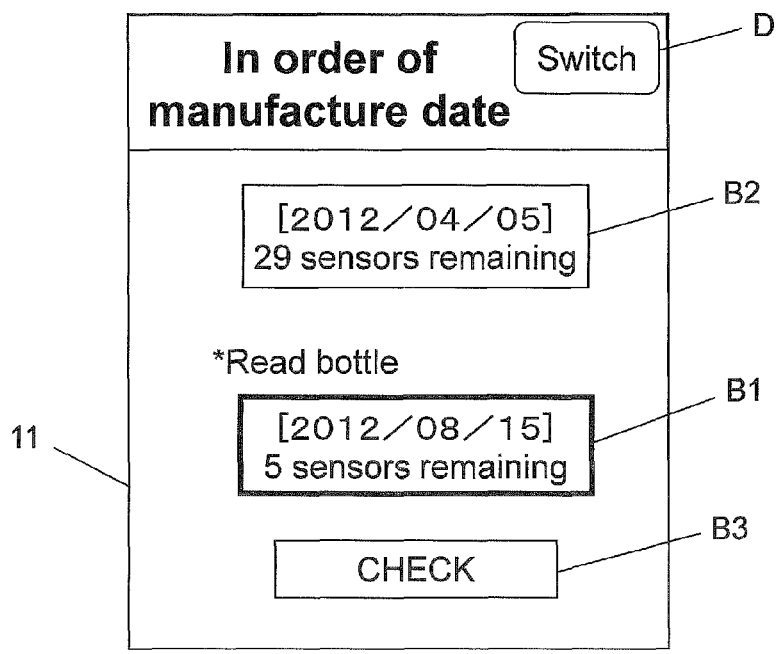
FIG. 28 is a diagram showing exemplary display by the display unit of the mobile terminal according to Embodiment 3.

In step S1311R in FIG. 21, the control unit 22 displays a bottle check screen in FIG. 27 or 28 on the display unit 11. FIGS. 27 and 28 are screens at the time when there are a plurality of sensor containers 201 in use and the sensor container 201 to be used is identified by reading the container information of the sensor container 201 that the user wants to use, using the barcode reading unit 23, and these screens correspond to FIG. 19 in Embodiment 2. Since the display of the display unit 11 in FIGS. 27 and 28 is also provided with the switching button D at the upper right of the screen, the control unit 22 can easily switch between the display in order of the use start date in FIG. 27 and the display in order of the manufacture date in FIG. 28.

Consequently, the user can easily identify the sensor container 201 that houses the sensors 2 with the earlier manufacture date, and the sensors 2 are made more user-friendly.

Note that the control unit 22 of the mobile terminal 8 in the present embodiment may display a notice based on the manufacture date of the sensors 2. Specifically, the control unit 22 reads today's date from the clock 30, and checks that today's date is smaller (earlier) than the validity expiration date of the sensors 2. This checking is performed when the number of sensors is displayed on the display unit 11, for example. If the validity expiration date of the sensors 2 is approaching, for example, if it is 20 days before the validity expiration date, the control unit 22 displays a notice (not shown) indicating that the validity expiration date is approaching, together with display of the number of sensors, via the display unit 11. Thus, since a notice is displayed on the display unit 11 if the validity expiration date of the sensors 2 is approaching, the user can see the displayed notice on the display unit 11 and become aware that the validity expiration date of the sensors 2 is approaching, and the sensors 2 are made more user-friendly in this aspect as well.

3-3 Effects Etc

As described above, with the sensor information management system 100 in the present embodiment, in addition to the effects of Embodiment 1 and/or Embodiment 2, the user can easily identify the sensor container 201 that houses the sensors 2 whose usable period will end sooner, and can also easily identify the sensor container 201 that houses the sensors 2 with the earlier manufacture date. Accordingly, the sensors 2 are made more user-friendly.

Other Embodiments

Embodiments 1 to 3 have been described thus far as examples of the technique disclosed in the present application. However, the technique described in the present disclosure is not limited thereto, and can also be applied to embodiments with appropriate modifications, substitutions, additions, omissions, or the like. Furthermore, a combination of the constituent elements described above in Embodiments 1 to 3 can also be used as a new embodiment.

Examples of other embodiments are described below.

[1]

Although barcode information is used as an example of the mark provided on the display part 5 so as to indicate the sensor information or the container information in the sensor containers 1 and 201 according to the above embodiments, this need not be the case. Other optically-readable marks, such as a QR code (registered trade mark), may be used. Alternatively, an identification code that can be read by communication, using an IC tag or the like, may be used.

[2]

Although the control unit 22 of the mobile terminal 8 displays the container information of the sensor containers 201 in order of the bottle use start date in the sensor information management system 100 according to Embodiment 2 described above, this need not be the case. The control unit 22 may display the container information of the sensor containers 201 in order of the manufacture date.

The embodiments have been described thus far as examples of the technique in the present disclosure. The attached drawings and detailed description have been provided for that purpose.

Accordingly, the constituent elements described in the attached drawings and the detailed description can include not only essential constituent elements for solving the problem but also constituent elements not essential for solving the problem, in order to describe examples of the technique. Therefore, it should not be immediately found that these unessential constituent elements are essential merely because these unessential constituent elements are described in the attached drawings or the detailed description.

Since the above embodiments are for describing examples of the technique in the present disclosure, various modifications, substitutions, additions, omissions, and the like may be made within the scope of claims or within an equivalent scope.

INDUSTRIAL APPLICABILITY

The technique according to the present disclosure is expected to be widely utilized as a sensor container for housing sensors for measuring, for example, a blood glucose level, a sensor information management method using the sensor container, and a sensor information management system for managing the sensors housed in the sensor container.

Reference Signs List
1 Sensor container
1A Sensor container
1B Sensor container
2 Sensor
3 Container
4 Lid
5 Display part
6 Label
7 Barcode
8 Mobile terminal
8a Body case
9 Measuring device
9a Body case
10 Display unit
11 Display unit
12 Seal
13 Puncture tool
14 Housing case
15 Sensor mount unit
16 Measurement unit
17 Control unit
18 Communication unit
19 Battery cell
20 Storage unit
21 Communication unit
22 Control unit
23 Barcode reading unit
24 Storage unit
25 Battery cell
26 Power key
27 Read button
28 Deposit unit
29 Bottle select icon
30 Clock
D Switching button

The invention claimed is:

1. A sensor container comprising:
a container body having an opening portion;
a lid configured to cover the opening portion of the container body;
one or more sensors configured to measure biological information, the one or more sensors being housed in the container body;
a mark indicating a usable period of the one or more sensors, the mark covered with a removable seal and disposed on either the container body or the lid;
the usable period starting from a point in time when the lid is released from the container body.

2. The sensor container according to claim 1, wherein:
the mark includes an optically-readable code.

3. The sensor container according to claim 1, wherein:
the seal includes a guidance prompting removal of the seal when use of the one or more sensors is to begin, the guidance disposed on a surface of the seal.

4. The sensor container according to claim 1, wherein:
the seal is arranged to span from the container to the lid.

5. The sensor container according to claim 1, wherein:
the mark further includes information indicating the number of sensors that are initially housed in the container body.

6. A method for managing sensor information of the sensor container according to claim 5, the method including:
reading sensor information, the sensor information including information indicating a usable period of the one or more sensors and information indicating the number of initially housed sensors; from the mark
storing the read sensor information in a storage unit;
updating the sensor information stored in the storage unit; and
displaying, on a display unit, the sensor information stored in the storage unit.

7. A sensor information management system comprising:
a sensor container according to claim 1;
a biological information measuring device configured to obtain a measured value; the one or more sensors housed in the sensor container configured to mount onto the biological information measuring device; and
a communication terminal configured to communicate with the biological information measuring device, and to receive the measured value from the biological information measuring device,
the communication terminal including:
a sensor information reading unit configured to read the mark on the sensor container;
a storage unit configured to store information acquired from the mark, the information indicating the usable period of the one or more sensors;
a display unit configured to display the usable period of the one or more sensors; and
a control unit operable to acquire the information indicating the usable period of the one or more sensors from the storage unit, and to cause the display unit to display the information.

8. A sensor information management system comprising:
the sensor container according to claim 5,
a biological information measuring device configured to obtain a measured value;
the one or more sensors housed in the sensor container configured to mount onto the biological information measuring device; and
a communication terminal configured to communicate with the biological information measuring device, and to receive the measured value from the biological information measuring device,
the communication terminal including:
a sensor information reading unit configured to read the mark on the sensor container;
a storage unit configured to store information acquired from the mark, the information indicating the usable period of the one or more sensors and the number of initially housed sensors;
a display unit configured to display the usable period of the sensors and the number of initially housed sensors; and
a control unit configured to acquire the information from the storage unit, and to cause the display unit to display the usable period of the one or more sensors and the number of initially housed sensors.

9. The sensor information management system according to claim 8, wherein:
the control unit of the communication terminal further causes the display unit to display a remaining number of sensors;
the remaining number of sensors being equal to the number of housed sensors less a number of times the control unit has received the measured value from the biological information measuring device.

10. A sensor information management system comprising:
a sensor container including a container body and a lid,
the container body including an opening,
the lid configured to cover the opening portion of the container body;
a biological information measuring device configured to obtain a measured value;
a plurality of sensors configured to measure biological information, and to mount onto the biological information measuring device, the plurality of sensors housed in the container body;
a mark including sensor information and disposed on the container body or the lid;
the sensor information including identification information of the sensor container, information indicating a number of sensors that are initially housed in the container body, and information indicating a usable period of the sensors starting from a point in time when the lid is released from the container body; and
a communication terminal including a sensor information reading unit, a storage unit, a display unit, and a control unit;
the reading configured to read the mark;
the storage unit configured to store the sensor information acquired from the mark;
the display unit configured to display the sensor information stored in the storage unit, and a control unit operable to acquire the sensor information from the storage unit and causes the display unit to display the acquired sensor information;
the communication terminal configured to:
communicate with the biological information measuring device;
receive the measured value from the biological information measuring device;
cause the storage unit to store the number of sensors, the number of sensors determined sensors being equal to the number of housed sensors less a number of times the control unit has received the measured value from the biological information measuring device; and
cause the display unit to display the acquired number of sensors.

11. The sensor information management system according to claim 10, wherein:
the communication terminal further includes a displayed execution operation unit; and
when the mark is read by the sensor information reading unit in accordance with an operation on the displayed execution operation unit, the control unit of the communication terminal causes the display unit to display the number of initially housed sensors in the sensor container having the read mark and a use start date of the sensor container.

12. The sensor information management system according to claim 11, wherein:
   the control unit of the communication terminal causes the display unit to display, as the use start date of the sensor container, a date of use of a sensor that was taken out of the container body before all of the other sensors.

13. The sensor information management system according to claim 12, wherein:
   the control unit of the communication terminal causes the display unit to display the number of sensors in one other sensor container and a use start date of the one other sensor container that are stored in the storage unit.

14. The sensor information management system according to claim 13, wherein:
   when the mark is read by the sensor information reading unit, the control unit of the communication terminal causes the number of sensors in the sensor container having the read mark and the use start date of the sensor container to be displayed in a user-specifiable manner on the display unit.

15. The sensor information management system according to claim 14, wherein:
   when the control unit of the communication terminal causes the display unit to display the number of sensors in a plurality of the sensor containers and the use start date of the sensor containers, the control unit causes the number of sensors and the use start date to be displayed in ascending order of the use start date of the sensors.

16. The sensor information management system according to claim 11, wherein:
   when the control unit of the communication terminal activates the sensor information reading unit in accordance with an operation on the displayed execution operation unit and reads the mark using the sensor information reading unit, the control unit causes the display unit to display the number of sensors in the sensor container having the read mark and an operation key for activating the sensor information reading unit.

17. The sensor information management system according to claim 16, wherein:
   when the control unit of the communication terminal activates the sensor information reading unit in accordance with an operation on the operation key and reads the mark using the sensor information reading unit, the control unit acquires, from the storage unit, the number of sensors in the sensor container having the read mark and the use start date of the sensor container, and causes the acquired number of sensors and use start date to be displayed in a user-specifiable manner on the display unit.

18. The sensor information management system according to claim 17, wherein:
   the control unit of the communication terminal is further configured to cause the display unit to display the number of sensors in an other sensor container and the use start date of the other sensor container that are stored in the storage unit.

19. The sensor information management system according to claim 11, wherein:
   the mark of the sensor container further includes information indicating a manufacture date of the sensors;
   the communication terminal further includes a displayed execution operation unit; and
   the control unit of the communication terminal is further configured to acquire information indicating the manufacture date of the sensors from the mark that is read by the sensor information reading unit, in accordance with an operation on the displayed execution operation unit, and to cause the display unit to display the manufacture date of the sensors.

20. The sensor information management system according to claim 19, wherein:
   when the mark is read by the sensor information reading unit, the control unit of the communication terminal causes the number of sensors in the sensor container having the read mark and the manufacture date of the sensors to be displayed in a user-specifiable manner on the display unit.

21. The sensor information management system according to claim 20, wherein:
   the control unit of the communication terminal causes the display unit to display the number of sensors in one other sensor container and the manufacture date of the sensors in the one other sensor container that are stored in the storage unit.

22. The sensor information management system according to claim 21, wherein:
   when the control unit of the communication terminal causes the display unit to display the number of sensors in a plurality of the sensor containers and the manufacture date of the sensors, the control unit causes the number of sensors and the manufacture date of the sensors to be displayed in ascending order of the manufacture date of the sensors.

23. The sensor information management system according to claim 22, wherein:
   when the control unit of the communication terminal activates the sensor information reading unit in accordance with an operation on the displayed execution operation unit, and the mark is read by the sensor information reading unit, the control unit causes the display unit to display the number of sensors in the sensor container having the read mark and the manufacture date of the sensors in the sensor container, together with an operation key for activating the sensor information reading unit.

24. The sensor information management system according to claim 23, wherein:
   when the control unit of the communication terminal activates the sensor information reading unit in accordance with an operation on the operation key, and the mark is read by the sensor information reading unit, the control unit acquires, from the storage unit, the number of sensors in the sensor container having the read mark and the manufacture date of the sensors in the sensor container, and causes the number of sensors and the manufacture date of the sensors to be displayed in a user-specifiable manner on the display unit.

25. The sensor information management system according to claim 24, wherein:
   the control unit of the communication terminal further causes the display unit to display the number of sensors in one other sensor container and the manufacture date of the sensors in the one other sensor container that are stored in the storage unit.

* * * * *